US008263760B2

(12) United States Patent
de Kimpe et al.

(10) Patent No.: US 8,263,760 B2
(45) Date of Patent: Sep. 11, 2012

(54) METHODS AND MEANS FOR TREATING DNA REPEAT INSTABILITY ASSOCIATED GENETIC DISORDERS

(75) Inventors: Josephus Johannes de Kimpe, Utrecht (NL); Gerardus Johannes Platenburg, Voorschoten (NL)

(73) Assignee: Prosensa Holding BV, Leiden (NL)

( * ) Notice: Subject to any disclaimer, the term of this patent is extended or adjusted under 35 U.S.C. 154(b) by 0 days.

(21) Appl. No.: 12/852,057

(22) Filed: Aug. 6, 2010

(65) Prior Publication Data

US 2011/0184050 A1  Jul. 28, 2011

Related U.S. Application Data

(63) Continuation of application No. PCT/NL2009/050049, filed on Feb. 5, 2009.

(30) Foreign Application Priority Data

Feb. 8, 2008 (EP) .................................... 08151228

(51) Int. Cl.
*C07H 21/04* (2006.01)
*C07H 21/02* (2006.01)
*C12N 15/63* (2006.01)
*A61K 48/00* (2006.01)

(52) U.S. Cl. ................... 536/24.5; 536/23.1; 536/24.31; 536/24.33; 435/320.1; 514/44

(58) Field of Classification Search ........................ None
See application file for complete search history.

(56) References Cited

U.S. PATENT DOCUMENTS

| | | | |
|---|---|---|---|
| 5,034,506 A | 7/1991 | Summerton et al. |
| 5,418,139 A | 5/1995 | Campbell |
| 5,541,308 A | 7/1996 | Hogan et al. |
| 5,593,974 A | 1/1997 | Rosenberg et al. |
| 5,608,046 A | 3/1997 | Cook et al. |
| 5,627,263 A | 5/1997 | Ruoslahti et al. |
| 5,658,764 A | 8/1997 | Pergolizzi et al. |
| 5,741,645 A | 4/1998 | Orr et al. |
| 5,766,847 A | 6/1998 | Jackle et al. |
| 5,853,995 A | 12/1998 | Lee |
| 5,869,252 A | 2/1999 | Bouma et al. |
| 5,962,332 A | 10/1999 | Singer et al. |
| 5,968,909 A | 10/1999 | Agrawal et al. |
| 6,124,100 A | 9/2000 | Jin |
| 6,130,207 A | 10/2000 | Dean et al. |
| 6,133,031 A | 10/2000 | Monia et al. |
| 6,172,216 B1 | 1/2001 | Bennett et al. |
| 6,251,589 B1 | 6/2001 | Tsuji et al. |
| 6,280,938 B1 | 8/2001 | Ranum et al. |
| 6,300,060 B1 | 10/2001 | Kantoff et al. |
| 6,322,978 B1 | 11/2001 | Kahn et al. |
| 6,329,501 B1 | 12/2001 | Smith et al. |
| 6,355,481 B1 | 3/2002 | Li et al. |
| 6,355,690 B1 | 3/2002 | Tsuji |
| 6,369,038 B1 | 4/2002 | Blumenfeld et al. |
| 6,379,698 B1 | 4/2002 | Leamon |
| 6,399,575 B1 | 6/2002 | Smith et al. |
| 6,514,755 B1 | 2/2003 | Ranum et al. |
| 6,623,927 B1 | 9/2003 | Brahmachari et al. |
| 6,653,466 B2 | 11/2003 | Matsuo |
| 6,653,467 B1 | 11/2003 | Matsuo et al. |
| 6,670,461 B1 | 12/2003 | Wengel et al. |
| 6,794,192 B2 | 9/2004 | Parums et al. |
| 6,902,896 B2 | 6/2005 | Ranum et al. |
| 6,982,150 B2 | 1/2006 | Sheetz et al. |
| 7,118,893 B2 | 10/2006 | Ranum et al. |
| 7,189,530 B2 | 3/2007 | Botstein et al. |
| 7,202,210 B2 | 4/2007 | Wolfman et al. |
| 7,250,404 B2 | 7/2007 | Felgner et al. |
| 2001/0056077 A1 | 12/2001 | Matsuo |
| 2002/0049173 A1 | 4/2002 | Bennett et al. |
| 2002/0055481 A1 | 5/2002 | Matsuo et al. |
| 2002/0115824 A1 | 8/2002 | Engler et al. |
| 2002/0165150 A1 | 11/2002 | Ben-Sasson |
| 2003/0073215 A1 | 4/2003 | Baker et al. |
| 2003/0082763 A1 | 5/2003 | Baker et al. |
| 2003/0082766 A1 | 5/2003 | Baker et al. |
| 2003/0109476 A1 | 6/2003 | Kmiec et al. |

(Continued)

FOREIGN PATENT DOCUMENTS

CA  2319149  10/2001

(Continued)

OTHER PUBLICATIONS

Aartsma-Rus et al. "Antisense Mediated exon skipping; A Versatile Tool with Therapeutic and Research Applications" *RNA* 2007 pp. 1609-1624 vol. 13 No. 10.
Aartsma-Rus et al. Antisense-Induced Exon Skipping for Duplications in Duchenne Muscular Dystrophy Jul. 5, 2007 BMC Med. Genet. 8:43.
Aartsma-Rus et al. Therapeutic Modulation of DMD splicing by Blocking Exonic Splicing Enhancer Sites with Antisense Oligonucleotides Ann NY Acad Sci 2006 pp. 74-76 vol. 1082.
Aartsma-Rus, et al., "Functional Analysis of 114 Exon-Internal AONs for Targeted DMD Exon Indication for Steric Hindrance of SR Protein Binding Sites," Oligonucleotides, 2005, pp. 284-297, vol. 15.
Aartsma-Rus, et al., Antisense-Induced Multiexon Skipping for Duchenne Muscular Dystrophy Makes More Sense, Am. J. Hum. Genet, 2004 pp. 83-92, vol. 74.
Aartsma-Rus, et al., Exploring the Frontiers of Therapeutic Exon Skipping for Duchenne Muscular Dystrophy by Double Targeting within One or Multiple Exons, Molecular Therapy, 2006, pp. 1-7.

(Continued)

*Primary Examiner* — Amy Bowman
(74) *Attorney, Agent, or Firm* — Elizabeth Spar; Kathleen Williams; Edwards Wildman Palmer LLP

(57) ABSTRACT

The current invention provides for methods and medicaments that apply an oligonucleotide comprising aninosine and/or an uracile and/or a nucleotide containing a base able to form a wobble base pair, said oligonucleotide being preferably RNAse H substantially independent and being complementary only to a repetitive sequence in a human gene transcript, for the manufacture of a medicament for the diagnosis, treatment or prevention of a cis-element repeat instability associated genetic disorders in humans. The invention hence provides a method of treatment for cis-element repeat instability associated genetic disorders. The invention also pertains to a modified oligonucleotide which can be applied in a method of the invention to prevent the accumulation and/or translation of repeat expanded transcripts in cells.

8 Claims, 5 Drawing Sheets

U.S. PATENT DOCUMENTS

Figure 1:
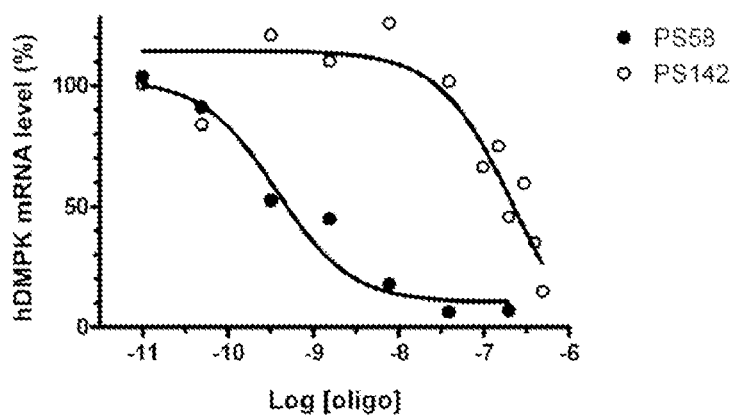

| | | | |
|---|---|---|---|
| 2003/0124523 A1 | 7/2003 | Asselbergs et al. |
| 2003/0134790 A1 | 7/2003 | Langenfeld |
| 2003/0235845 A1 | 12/2003 | van Ommen et al. |
| 2003/0236214 A1 | 12/2003 | Wolff et al. |
| 2004/0101852 A1 | 5/2004 | Bennett et al. |
| 2004/0132684 A1 | 7/2004 | Sampath et al. |
| 2004/0226056 A1 | 11/2004 | Roch et al. |
| 2005/0096284 A1 | 5/2005 | McSwiggen |
| 2005/0222009 A1 | 10/2005 | Lamensdorf et al. |
| 2005/0246794 A1 | 11/2005 | Khvorova et al. |
| 2005/0277133 A1 | 12/2005 | McSwiggen |
| 2006/0074034 A1 | 4/2006 | Collins et al. |
| 2006/0148740 A1 | 7/2006 | Platenburg |
| 2007/0082861 A1 | 4/2007 | Matsuo et al. |
| 2007/0275914 A1* | 11/2007 | Manoharan et al. ............ 514/44 |
| 2007/0292408 A1 | 12/2007 | Singh et al. |
| 2008/0015158 A1 | 1/2008 | Ichiro et al. |

FOREIGN PATENT DOCUMENTS

| | | |
|---|---|---|
| CA | 2526893 | 11/2004 |
| EP | 438512 A1 | 7/1991 |
| EP | 558697 | 9/1993 |
| EP | 614977 A2 | 9/1994 |
| EP | 850300 | 7/1998 |
| EP | 1054058 | 5/2000 |
| EP | 1015628 A1 | 7/2000 |
| EP | 1133993 | 9/2001 |
| EP | 1160318 | 12/2001 |
| EP | 1191097 | 3/2002 |
| EP | 1191098 | 3/2002 |
| EP | 1380644 | 1/2004 |
| EP | 1 487 493 A2 | 12/2004 |
| EP | 1495769 | 1/2005 |
| EP | 1501931 | 2/2005 |
| EP | 1544297 | 6/2005 |
| EP | 1567667 A1 | 8/2005 |
| EP | 1568769 | 8/2005 |
| EP | 1619249 | 1/2006 |
| EP | 1857548 | 11/2007 |
| KR | 20030035047 | 5/2003 |
| WO | WO-9301286 A2 | 1/1993 |
| WO | WO-95/16718 A1 | 6/1995 |
| WO | 95/30774 | 11/1995 |
| WO | WO-9712899 | 4/1997 |
| WO | WO-9730067 | 8/1997 |
| WO | WO-9818920 A1 | 5/1998 |
| WO | WO-9849345 A1 | 11/1998 |
| WO | WO-0179283 A1 | 10/2001 |
| WO | WO-0183695 | 11/2001 |
| WO | WO-0202406 | 1/2002 |
| WO | WO-0224906 | 3/2002 |
| WO | WO-0226812 A1 | 4/2002 |
| WO | WO-0229056 | 4/2002 |
| WO | WO-03002739 | 1/2003 |
| WO | 03/013437 A2 | 2/2003 |
| WO | WO-03/14145 A2 | 2/2003 |
| WO | WO-03037172 | 5/2003 |
| WO | WO-03095647 | 11/2003 |
| WO | WO-2004/011060 A2 | 2/2004 |
| WO | WO-2004015106 | 2/2004 |
| WO | WO-2004016787 | 2/2004 |
| WO | WO-2004048570 | 6/2004 |
| WO | WO-2004083432 | 9/2004 |
| WO | WO-2004083446 | 9/2004 |
| WO | WO-2004101787 | 11/2004 |
| WO | WO-2004108157 | 12/2004 |
| WO | WO-2004108157 A2 | 12/2004 |
| WO | WO-2005019453 A2 | 3/2005 |
| WO | WO-2005035550 | 4/2005 |
| WO | WO-2005085476 A1 | 9/2005 |
| WO | WO-2005086768 | 9/2005 |
| WO | WO-2005105995 A2 | 11/2005 |
| WO | WO-2005115439 | 12/2005 |
| WO | WO-2005116204 A1 | 12/2005 |
| WO | WO-2006000057 | 1/2006 |
| WO | WO-2006007910 | 1/2006 |
| WO | WO-2006017522 | 2/2006 |
| WO | 2006/031267 A2 | 3/2006 |
| WO | WO-2006/054262 A2 | 5/2006 |
| WO | 2006/083800 A2 | 8/2006 |
| WO | WO-2006108052 | 10/2006 |
| WO | WO-2006112705 | 10/2006 |
| WO | WO-2006121960 A2 | 11/2006 |
| WO | WO-2007002904 A2 | 1/2007 |
| WO | 2007/044362 A2 | 4/2007 |
| WO | WO-2007089584 | 8/2007 |
| WO | WO-2007089611 A2 | 8/2007 |
| WO | WO-2007123402 | 11/2007 |
| WO | WO-2007135105 | 11/2007 |
| WO | WO-2008011170 A2 | 1/2008 |
| WO | 2008/018795 A1 | 2/2008 |

OTHER PUBLICATIONS

Aartsma-Rus, et al., Targeted exon skipping as a potential gene correction therapy for Duchenne muscular dystrophy, Neuromuscular Disorders, 2002, S71-S77, vol. 12.

Aartsma-Rus, et al., Therapeutic antisense-induced exon skipping in cultured muscle cells from six different patients, Human Molecular Genetics, 2003, pp. 907-914, vol. 12, No. 8.

Abbs et al., A convenient multiplex PCR system for the detection of dystrophin gene deletions: a comparative analysis with cDNA hybridisation shows mistypings by both methods, J. Med. Genet, 1991, pp. 304-311, vol. 28.

Agrawal and Kandimalla, et al., "Antisense therapeutics: is it as simple as complementary base recognition?" Mol. Med. Today, Feb. 2000, vol. 6., pp. 72-81.

Anderson et al., Correlated NOS-I[mu] and myf5 expression by satellite cells in mdx mouse muscle regeneration during NOS manipulation and deflazacort treatment. Neuromusccular Disorders, Jun. 2003, vol. 13(5): 388-396.

Arechavala-Gomeza et al., . "Comparative Analysis of Antisense Oligonucleotide Sequences for Targeted Skipping of Exon 51 During Dystrophin pre-mRNA Splicing in Human Muscle" *Hum Gene Ther 2007* pp. 798-810 vol. 18 No. 9.

Arruda V R, The role of immunosuppression in gene and cell based treatments for Duchenne Muscular Dystrophy. Molecular Therapy, Jun. 2007, vol. 15(6): 1040-1041.

Arzumanov, et al. Inhibition of HIV-1 Tat-dependent trans activation by steric block chimeric 2'-O-methyl/LNA oligoribonucleotides. Biochemistry, 2001, vol. 40, pp. 14645-14654.

Austin et al. "Cloning and characterization of alternatively spliced isoforms of Dp71." *Hum Mol Genetics* 1995 vol. 4 No. 9 1475-1483.

Austin, et al., "Expression and synthesis of alternatively spliced variants of Dp71 in adult human brain." *Neuromuscular Disorders*. 10(2000) 187-193.

Australian Office Action for AU 2009240879, dated Jun. 22, 2011.

Barabino et al. (1992) "Antisense probes targeted to an internal domain in US snRNP specifically inhibit the second step of pre-mRNA splicing" Nucleic Acids Res. 20(17):4457-4464.

Bionity.Com NEWS-Center, Leiden University Medical Center and Prosensa B.V. Announce First Successful Clinical Study with RNA-based Therapeutic PRO051, dated Jan. 3, 2008, <http://www.bionity.com/news/e/76185>.

Biopharmaceutiques, Merging Pharma & Biotech, Edition 48, Jan. 10, 2008. <http://www.biopharmaceutiques.com/en/num>, visited Jan. 11, 2008.

Bremmer-Bout, et al., Targeted exon skipping in transgenic hDMD mice: A model for direct preclinical screening of human-specific antisense oligonucleotides. Mol Ther. Aug. 2004; 10(2):232-40.

Brett et al., EST comparison indicates 38% of human m RNAs contain possible alternative splice forms. FEBS Lett 474(1): 83-86.

Brown, et al., "Structure and mutation of the dystrophin gene" in Dystrophin: Gene, protein and cell biology, (Brown and Lucy, eds). Cambridge University Press, Cambridge, 1997, pp. 1-16.

Burnett, et al., "DNA sequence-specific polyamides alleviate transcription inhibition associated with long GAA. TTC repeats in Friedreich's ataxia," *PNAS*, 2006, pp. 11497-11502, vol. 103, No. 31.

Canadian Office Action for CA 2,524,255, dated Jul. 6, 2011.

Caplen, et al., "Rescue of polyglutamine-mediated cytotoxicity by double-stranded RNA-mediated RNA interference," *Human molecular genetics*, 2002, pp. 175-184, vol. 11, No. 2.

Cartegni, et al., Abstract, Listening to silence and understanding nonsense: exonic mutations that affect splicing, Nature Reviews Genetics, Apr. 2002, pp. 285-298, vol. 3.

Chaubourt et al., Muscular nitric oxide synthase ([mu]NOS) and utrophin. J. of Physiology Paris, Jan.-Mar. 2002; vol. 96(1-2): 43-52.

Coulter et al. Identification of a new class of exonic splicing enhancers by in vivo selection. Mol. Cell. Biol. 17(4) 2143-50 (1997).

Crooke. In Basic Principles of Antisense Therapeutics, Springer-Verlag, Eds, New York, 1998, pp. 1-50.

Dahlqvist, et al., "Functional notch signaling is required for BMP4-induced inhibition of myogenic differentiation," Development 130:6089-6099 (2003).

De Angelis, et al., Chimeric snRNA molecules carrying antisense sequences against the splice junctions of exon 51 of the dystrophin pre-mRNA exon skipping and restoration of a dystrophin synthesis in delta 48-50 DMD cells, PNAS, Jul. 9, 2002, pp. 9456-9461, vol. 99, No. 14.

Declaration of Dr. Adrian Krainer (submitted in Third Party's Stmt for JP Appl. No. 2002-529499, dated Oct. 29, 2010).

Dickson, et al., Screening for antisense modulation of dystrophin pre-mRNA splicing, Neuromuscul. Disord., 2002, S67-70, Suppl. 1.

Dirkson, et al., Mapping the SF2/ASF Binding Sites in the Bovine Growth Hormone Exonic Splicing Enhancer, The Journal of Biological Chemistry, Sep. 15, 2000, pp. 29170-29177, vol. 275, No. 37.

Dunckley, et al., Modification of splicing in the Dsytrophin gene in cultured Mdx muscle cells by antisense oligoribonucleotides. Hum Mol Genet. 1995 7(7):1083-90.

Dunckley, et al., Modulation of Splicing in the DMD Gene by Antisense Oligoribonucleotides, Nucleosides & Nucleotides, 1997, pp. 1665-1668, vol. 16, No. 7-9.

Erba et al., Structure, chromosome location, and expression of the human gamma-actin gene: differential evolution, location, and expression of the cytoskeletal beta- and gamma-actin genes. Mol. Cell. Biology, 1988, 8(4):1775-89.

Errington, et al., Target selection for antisense oligonucleotide induced exon skipping in the dystrophin gene. J Gene Med. Jun. 2003; 5(6):518-27.

European Patent Office Action dated Jan. 29, 2007.

Feener et al., Alternative splicing of human dystrophin mRNA generates isoforms at the carboxy terminus. Nature, 338 (6215): 509-511 (1989).

Fluiter, K., "In Vivo tumor growth inhibition and biodistribution studies of locked nucleic acid (LNA) antisense oligonucleotides," Nucl. Acids Research 2003, vol. 31., No. 3., pp. 953-962.

Galderisi, et al., "Myotonic dystrophy: antisense oligonucleotide inhibition of DMPK gene expression in vitro." Biochem Biophys Res Commun 221:750-754 (1996).

Genes VII, Jan. 2000, Benjamin Lewin, Chapter 22, Nuclear Splicing, pp. 704-705.

Ginjaar, et al., Dystrophin nonsense mutation induces different levels of exon 29 skipping and leads to variable phenotypes within one BMD family, European Journal of Human Genetics (2000) 8, 793-796.

Grady, "Early drug test shows promise in treating muscular dystrophy" International Herald Tribune, Jan. 3, 2008, Health & Science, p. 9.

Grady, Promising Dystrophy Drug Clears Early Test, The New York Times, Dec. 27, 2007.

Granchelli et al., Pre-clinical screening of drugs using the mdx mouse. Neuromuscular Disorders, Pergamon Pres. vol. 10(4-5): 235-239, Jun. 2000.

Gryaznov, "Oligonucleotide N3'→ P5' phosphoramidates as potential therapeutic agents." Biochemistry et Biophys. Acta, 1999, vol. 1489, pp. 131-140/.

Hagiwara, et al. "A novel point mutation (G-1 to T) in a 5' splice donor site of intron 13 of the dystrophin gene results in exon skipping and is responsible for Becker muscular dystrophy." Am J. Hum Genet. Jan. 1994;54(1):53-61.

Handa, et al., "The AUUCU repeats responsible for spinocerebellar ataxia type 10 form unusual RNA hairpins." Journal of Biological Chemistry 280(32):29340-29345 (2005).

Hansen, "Product Development—Addition by subtraction." BioCentury, The Bernstein Report on BioBusiness, Jan. 7, 2008, p. A28 of 38.

Hasholt, et al., "Antisense downregulation of mutant huntingtin in a cell model," Journal of Gene Medicine, 2003, pp. 528-538, vol. 5, No. 6.

Hoffman, et al., "Somatic reversion/suppression of the mouse mdx phenotype in vivo." J. of the Neurological Sciences, 1990, 99: 9-25.

Hoffman, Skipping toward Personalized Molecular Medicine, N. England J. Med., Dec. 27, 2007, pp. 2719-2722, vol. 357, No. 26.

Hope for muscular dystrophy drug, The Daily Telegraph, Dec. 28, 2007.

Hussey, et al., Analysis of five Duchenne muscular dystrophy exons and gender determination using conventional duplex polymerase chain reaction on single cells, Molecular Human Reproduction, 1999, pp. 1089-1094, vol. 5, No. 11.

Iezzi, et al. "Deacetylase inhibitors increase muscle cell size by promoting myoblast recruitment and fusion through induction of follistation," Development Cell 6:673-684 (2004).

International Preliminary Examination Report, International Application No. PCT/NL01/00697, dated Aug. 1, 2002.

International Search Report, International Application No. PCT/NL2008/050470, dated Jul. 2, 2009.

International Search Report, International Application No. PCT/NL2008/050475, dated Jun. 25, 2009.

International Search Report, International Application No. PCT/NL2008/050673, dated Feb. 9, 2009.

International Search Report, International Application No. PCT/NL01/00697, dated Dec. 21, 2002.

International Search Report, International Application No. PCT/NL2004/000196, dated Oct. 28, 2004.

International Search Report, International Application No. PCT/NL2006/000209, dated Oct. 5, 2006.

International Search Report, International Application No. PCT/NL2009/050006, dated Jul. 31, 2009.

International Search Report, International Application No. PCT/NL2009/050113, dated Jun. 30, 2010.

Karras, et al., Deletion of Individual Exons and Induction of Soluble Murine Interleukin-5 Receptor-alpha Chain Expression through Antisense Oligonucleotide-Mediated Redirection of Pre-mRNA Splicing, Molecular Pharmacology, 2000, pp. 380-87, vol. 58.

Kerr, et al., "Bmp Regulates Skeletal Myogenesis at Two Steps," Molecular Cellular Proteomics 2.9:976. 123.8 (2003) (Abstract Only).

Kurrek, et al., "Design of antisense oligonucleotides stabilized by locked nucleic acids." Nucleic Acids Research, 2002, vol. 30, No. 9, pp. 1911-1918.

Langlois, et al., "Hammerhead ribozyme-mediated destruction of nuclear foci in myotonic dystrophy myoblasts," Molecular therapy, 2003, pp. 670-680, vol. 7, No. 5.

Laptev et al., (1994) "Specific inhibition of expression of a human collagen gene (COL1A1) with modified antisense oligonucleotides. The most effective target sites are clustered in double-stranded regions of the predicted secondary structure for the mRNA" Biochemistry 33(36):11033-11039.

Lee et al., "Receptor mediated uptake of peptides that bind the human transferrin receptor", Eur. J. Biochem. 268, 2004-2012 (2001).

Leiden University Medical Center and Prosensa B.V. Announce New England Journal of Medicine Publication of First Successful Clinical Study with RNA-based Therapeutic PRO051 in Duchenne Muscular Dystrophy, Dec. 27, 2007.

Letter from Katholieke Universiteit Leuven to Dr. N. Goemans, Child Neurology, UZ dated Jan. 22, 2008, regarding a Phase I/II, open label, escalating dose, pilot study to assess the effect, safety, tolerability and pharmacokinetics of multiple subcutaneous doses of PRO051 in patients with Duchenne muscular dystrophy. PRO051-02 (translation provided).

Letter from Prosensa Therapeutics B.V. to Federal Agency for Medicines and Health Products dated Jan. 9, 2008, regarding a Phase I/II, open label, escalating dose, pilot study to assess the effect, safety, tolerability and pharmacokinetics of multiple subcutaneous doses of PRO051 in patients with Duchenne muscular dystrophy.

Liu et al., "A mechanism for exon skipping caused by nonsense or missense mutations in BRCA1 and other genes." Nat Genet. Jan. 2001; 27(1):55-8.

Liu, et al., Identification of functional exonic splicing enhancer motifs recognized by individual SR proteins, Genes & Development, 1998, pp. 1998-2012, vol. 12.

Lu et al. Functional Amounts of Dystrophin Produced by Skipping the Mutated Exon in the MDX Dystrophic Mouse 2003 Nat Med 8: 1009-1014.

Lu, et al., Massive Idiosyncratic Exon Skipping Corrects the Nonsense Mutation in Dystrophic Mouse Muscle and Produces Functional Revertant Fibers by Clonal Expansion, The Journal Cell Biology, Mar. 6, 2000, pp. 985-995, vol. 148, No. 5.

LUMC and Prosensa report positive results of DMD study, Pharmaceutical Business Review Online, dated Dec. 28, 2007, <http://www.pharmaceutical-business-review.com/article_news_printasp?guid=8462FD44-F35D-4EOB-BC>.

Mann, et al., Antisense-induced exon skipping and synthesis of dystrophin in the mdx mouse. Proc Natl Acad Sci USA Jan. 2, 2001: 98(1):42-7.

Mann, et al., Improved antisense oligonucleotide induced exon skipping in the mdx mouse model of muscular dystrophy. J Gene Med. Nov.-Dec. 2002:4(6):644-54.

Matsuo et al. (1992) "Partial deletion of a dystrophin gene leads to exon skipping and to loss of an intra-exon hairpin structure from the predicted mRNA precursor" Biochem. Biophys. Res. Commun. 182(2):495-500.

Matsuo, et al., "Duchenne/Becker muscular dystrophy: from molecular diagnosis to gene therapy." Brain Dev. (1996) 18(3):167-172.

Matsuo, et al., Exon Skipping during Splicing of Dystrophin mRNA Precursor due to an Intraexon Deletion in the Dystrophin Gene of Duchenne Muscular Dystrophe Kobe. J. Clin. Invest. 87, 2127-2131.

McClorey et al. Induced Dystrophin Exon Skipping in Human Muscle Explants Neuromuscul Disord 2006 pp. 583-590 vol. 16 No. 9-10.

Monaco, et al., An Explanation for the Phenotypic Differences between Patients Bearing Partial Deletions of the DMD Locus, Genomics, 1988, pp. 90-95, vol. 2.

Moon, et. al., "Target site Search and effective inhibition of leukaemic cell growth by a covalently closed multiple anti-sense oligonucleotide to c-myb" The Biochemical Journal, Mar. 1, 2000, vol. 346 Pt 2, pp. 295-303.

Munroe (1988) "Antisense RNA inhibits splicing of pre-mRNA in vitro" EMBO J. 7(8):2523-2532.

Muntoni et al. "A Mutation in the Dystrophin Gene Selectively Affecting Dystrophin Expression in the Heart." J. Clin Invest. vol. 96 Aug. 1995. 693-699.

Muntoni, et al., 149th ENMC International Workshop and 1st TREAT-NMD Workshop on: "Planning Phase I/II Clinical trials using Systemically Delivered Antisense Oligonucleotides in Duchenne Muscular Dystrophy," Neuromuscular Disorders, 2008, pp. 268-275, vol. 18.

New Clinical Trial Results Show How Personalized Medicine Will Alter Treatment of Genetic Disorders, Medical News Today, Dec. 29, 2007 <http://www.medicalnewstoday.com/article/92777.php>.

Nishio, et al., Identification of a novel first exon in the human dystrophin gene and of a new promoter located more than 500 kb upstream of the nearest known promoter. (1994) J. Clin. Invest. 94:1037-1042.

Notice of Opposition filed against EP 1 619 249 B, dated Jun. 23, 2009.

Office Action for U.S. Appl. No. 10/395,031, dated Apr. 2, 2009.
Office Action for U.S. Appl. No. 10/395,031, dated Aug. 23, 2007.
Office Action for U.S. Appl. No. 10/395,031, dated Feb. 6, 2006.
Office Action for U.S. Appl. No. 10/395,031, dated Jul. 8, 2005.
Office Action for U.S. Appl. No. 10/395,031, dated May 30, 2008.
Office Action for U.S. Appl. No. 10/395,031, dated Nov. 30, 2006.
Office Action for U.S. Appl. No. 10/395,031, dated Oct. 16, 2009.
Office Action for U.S. Appl. No. 11/233,495, dated Dec. 1, 2008.
Office Action for U.S. Appl. No. 11/233,495, dated Jun. 25, 2009.
Office Action for U.S. Appl. No. 11/233,507, dated Jun. 15, 2007.
Office Action for U.S. Appl. No. 11/233,507, dated Mar. 19, 2008.
Office Action for U.S. Appl. No. 11/233,507, dated May 29, 2009.
Office Action for U.S. Appl. No. 11/233,507, dated Nov. 12, 2008.
Office Action for U.S. Appl. No. 11/982,285, dated May 4, 2009.
Office Action for U.S. Appl. No. 11/982,285, dated Sep. 18, 2009.

Opalinska and Gewirtz. "Nucleic-acid therapeutics: basic principles and recent applications." Nature Reviews Drug Discovery, 2002, vol. 1, pp. 503-514.

Oxford Dictionary of English, 2nd Edition, Revised, Oxford University Press, p. 158.

Patel, et al., "The Function of Myostatin and strategies of Myostatin blockade-new hope for therapies aimed at promoting growth of skeletal muscle," Neuromuscular Disorders 15(2):117-126 (2005).

Patentee's response during prosecution of opposed patent, dated Jan. 27, 2010.

Pramono, et al., Abstract, Induction of Exon Skipping of the Dystrophin Transcript in Lymphoblastoid Cells by Transfecting an Antisense Oligodeoxynucleotide Complementary to an Exon Recognition Sequence, Biochemical and Biophysical Research Communications, Sep. 13, 1996, pp. 445-449, vol. 226, No. 2.

Radley et al., Duchenne muscular dystrophy: Focus on pharmaceutical and nutritional interventions. International J. of Biochem. and Cell Biol., vol. 39(3):469-477, Oct. 2006.

Rando, Thomas A., "Oligonucleotide-mediated gene therapy for muscular dystrophies." Neuromuscular Disorders, 2002, vol. 12, pp. S55-S60.

Request for an Opinion under Section 74(A) in relation to Patent No. EP (UK) 1 619 249B in the name of Academisch Ziekenhuis Leiden, opinion issued on Jun. 4, 2009.

Request for UK IPO Opinion (Section 74A & Rule 93)—EP(UK) 1619249 dated Mar. 9, 2009.

Roberts et al., Direct detection of dystrophin gene rearrangements by analysis of dystrophin mRNA in peripheral blood lymphocytes. Am. J. Hum. Genet. 49(2): 298-310 (1991).

Roberts, et al., "Exon structure of the human dystrophin gene." Genomics, 1993, vol. 16, No. 2, pp. 536-538. (1993).

Roberts, et al., Direct diagnosis of carriers of Duchenne and Becker muscular dystrophy by amplification of lymphocyte RNA. Lancet, 336 (8730-8731): 1523-6 (1990).

Roberts, et al., Searching for the 1 in 2,400,000: a review of dystrophin gene point mutations. Hum. Mut. 4:1-11 (1994).

Rolland et al., Overactivity of exercise-sensitive cation channels and their impaired modulation by IGF-1 in mdx native muscle fibers: beneficial effect of pentoxifylline. Dec. 2006; Epub Sep. 28, Neurobiology Disease, vol. 24(3): 466-474.

Scanlon, "Anti-genes: siRNA, ribozymes, and antisense." Curr. Pharmaceutical Biotechnology, 2004, vol. 5, pp. 415-420.

Segalat et al., Capon expression in skeletal muscle is regulated by position, repair, NOS activity, and dystrophy. Experimental Cell Research, Jan. 2005, vol. 302(2): 170-179.

Sertic, et al., "Deletion screening of the Duchenne/Becker muscular dystrophy gene in Croatian population" Coll. Antropol. 1997, 1:151-156.

Shapiro and Senapathy, "RNA splice junctions of different classes of eukaryotes: sequence statistics and functional implications in gene expression." Nucleic Acids Research, 1987, vol. 15. No. 17, pp. 7155-7174.

Sherratt, et al., Exon Skipping and Translation in Patients with Frameshift Deletions in the Dystrophin Gene, Am. J. Hum. Genet, 1993, pp. 1007-1015, vol. 53.

Shiga, et al., Disruption of the Splicing Enhancer Sequence within Exon 27 of the Dystrophin Gene by a Nonsense Mutation Induces Partial Skipping of the Exon and Is Responsible for Becker Muscular Dystrophy, J. Clin. Invest., Nov. 1997, pp. 2204-2210, vol. 100, No. 9.

Simoes-Wust, et al., bcl-xL Antisense Treatment Induces Apoptosis in Breast Carcinoma Cells, Int. J. Cancer, 2000, pp. 582-590, vol. 87.

Sterrenburg, et al., "Gene expression of profiling highlights defective myogenesis in DMD patients and a possible role for bone morphogenetic protein 4," Neurobiology of Disease 23(1):228-236 (2006).

Surono et al. Chimeric RNA/ethylene-Bridged Nucleic Acids Promote Dystrophin Expression in Myocytes of Duchenne Muscular Dystrophy by Inducing Skipping of the Nonsense Mutation-Encoding Exon Hum Gene Ther. vol. 15(8) pp. 749-757 (2004).

Surono et al. "Six Novel Transcripts that Remove a Huge Intron Ranging from 250 to 800 kb Are Produced by Alternative Splicing of the 5' Region of the Dystrophin Gene in Human Skeletal Muscle." *BBRC* 239 895-899 (1997).

Suter, et al., Double-target antisense U7 snRNAs promote efficient skipping of an aberrant exon in three human B-thalassemic mutations, Human Molecular Genetics, 1999, pp. 2415-2423, vol. 8, No. 13.

Suwanmanee et al. (2002) "Restoration of Human b-globin Gene Expression in Murine and Human IVS2-654 Thalassemic Erythroid Cells by Free Uptake of Antisense Oligonucleotides" Mol. Pharmacology 62(3):545-553.

Takashima et al. Oligonucleotides Against a Splicing Enhancer Sequence Led to Dystrophin Production in Muscle Cells From a Duchenne Muscular Dystrophy Patient Brain Dev Dec. 2001; 23:788-90.

Takeshima, et al., Modulation of In Vitro Splicing of the Upstream Intron by Modifying an Intra-Exon Sequence Which is Deleted from the Dystrophin Gene in Dystrophin Kobe, J. Clin. Invest., Feb. 1995, pp. 515-520, vol. 95.

Tanaka, et al., Polypurine Sequences within a Downstream Exon Function as a Splicing Enhanced, Molecular and Cellular Biology, Feb. 1994, pp. 1347-1354, vol. 14, No. 2.

Thanh, et al., "Characterization of revertant muscle fibers in Duchenne muscular dystrophy, using exon-specific monoclonal antibodies against dystrophin." Am. J. Hum. Genet. 1995, vol. 56, pp. 725-731.

Third Party's Statement for Japan Appl. No. 2002-529499, dated Oct. 29, 2010.

Tian H, Kole R, "Selection of novel exon recognition elements from a pool of random sequences." Mol Cell Biol 15(11):6291-8. (1995).

TREAT-NMD Neuromuscular Network, Jan. 11, 2008.

Tsuchida "Peptides, Proteins & Antisense: the role of myostatin and bone morphogenetic proteins in muscular disorders," Expert Opinion of Biologica Therapy 6(2):147-153 (2006).

Van Deutekom et al. Advances in Duchenne Muscular Dystrophy Gene Therapy 2003 Nat Rev Genet 4(10): 774-83.

Van Deutekom, et al., Antisense-induced exon skipping restores dystrophin expression in DMD patient derived muscle cells. Hum Mol Genet. Jul. 15, 2001:10(15:1547-54).

Van Deutekom, et al., Local Dystrophin Restoration with Antisense Oligonucleotide PRO051, N. England J. Med., Dec. 27, 2007, pp. 2677-2686.

Van Ommen "The Therapeutic Potential of Antisense-Mediated Exon-Skipping." Curr Opin Mol. Ther vol. 10(2) pp. 140-149. 2008.

Verreault, et al. "GENE silencing in the development of personalized cancer treatment: the targets, the agents and the delivery systems." Curr. Gene Therapy, 2006, vol. 6, pp. 505-553.

Vickers, et al., "Efficient reduction of target RNAs by small interfering RNA and RNase H-dependent antisense agents. A comparative analysis." *J. Biol. Chem.* 278(9):7108-7118 (2003).

Watakabe, et al., The role of exon sequences in splice site selection, Genes & Development, 1993, pp. 407-418, vol. 7.

Wells et al. Enhanced in Vivo Delivery of Antisense Oligonucleotide to Restore Dystrophin Expression in Adult MDX Mouse Muscle FEBS Letters 2003 552: 145-149.

Wheway and Roberts. "The Dystrophin Lymphocyte promoter revisited: 4.5-megabase intron, or artefact?" *Neuromuscular Disorders* 13(2003) 17-20.

Wilton, et al., "Specific removal of the nonsense mutation from the mdx dystrophin protein mRNA using antisense oligonucleotides." Neuromuscular Disorders, 1999, vol. 9, pp. 330-338.

Wilton, et al., "Antisense oligonucleotide-induced exon skipping across the human dystrophin gene transcript." Mol Ther. Jul. 2007;15(7):1288-96.

Wilton, et al., "Antisense oligonucleotides, exon skipping and the dystrophin gene transcript," Acta Myologica XXIV:222-229 (2005).

Yen, et al., "Sequence-specific cleavage of Huntingtin MRNA by catalytic DNA," *Animals of Neurology*, 1999, pp. 366-373, vol. 46, No. 3.

Zhou et al., Current understanding of dystrophin-related muscular dystrophy and therapeutic challenges ahead. Chinese Medical J., Aug. 2006, vol. 119(16): 1381-1391.

Furling et al., "Viral vector producing antisense RNA restores myotonic dystrophy myoblast functions", Gene Therapy (2003) 10, 795-802.

Liu et al., "Specific inhibition of Huntington's disease gene expression by siRNAs in cultured cells", Proc. Japan Acad., 79, Ser. B (2003), 293-298.

Buck et al., "Design Strategies and Performance of Custom DNA Sequencing Primers" *Biotechniques.* 27:528-536, 1999.

Duboc et al., "Effect of Perindopril on the Onset and Progression of Left Ventricular Dysfunction in Duchenne Muscular Dystrophy." *Journal of Amer. Coll. Cardiology*, 45(6):855-7, Mar. 15, 2005.

GenBank accession No. AZ993191.1, 2MO278E12F mouse 10kb plasmid UUGC2M library Mus muscu genomic clone UUGC2MO278E12F, genomic survey sequence, entry created and last updated on Apr. 27, 2001.

GenBank accession No. EW162121.1, rfat0126_k17.y1 fat Sus scrofa cDNA5-, mRNA sequence, entry created on Aug. 13, 2007, last updated on Mar. 3, 2011.

Ikezawa et al. "Dystrophin gene analysis on 130 patients with Duchenne Muscular dystrophy with a special reference to muscle mRNA analysis." *Brain & Develop.* 20:165-168, 1998.

International Preliminary Report on Patentability and Written Opinion for PCT/EP2007/054842, mailed on Nov. 21, 2008, 8 pages.

International Search Report for PCT/EP2007/054842, mailed on Aug. 21, 2007, 3 pages.

Letter from Katholieke Universiteit Leuven to Dr. N. Goemans, Child Neurology, UZ dated Jan. 22, 2008, regarding a Phase I/II, open label, escalating dose, pilot study to assess the effect, safety, tolerability and pharmacokinetics of multiple subcutan.

O'Shaughnessy et al., "Superior Survival With Capecitabine Plus Docetaxel Combination Therapy in Anthracycline-Pretreated Patients With Advanced Breast Cancer: Phase III Trial Results." *Journal of Clinical Oncology*, vol. 20, No. 12 Jun. 15, 2002: pp. 2812-2823.

Rosen et al., "Combination Chemotherapy and Radiation Therapy in the Treatment of Metastatic Osteogenic Sarcoma." *Cancer* 35: 622-630, 1975.

Takeshima et al "Intravenous Infusion of an Antisense Oligonucleotide Results in Exon Skipping in Muscle Dystrophin mRNA of Duchenne Muscular Dystrophy." *Pediatric Research*. May 2006, 59, 5, p. 690-694.

Verhaart et al., "Prednisolone treatment does not interfere with 2'-O-methyl phosphorothioate antisense-mediated exon skipping in Duchenne muscular dystrophy." *Hum Gene Ther*. Mar. 2012;23(3):262-73. Epub Jan. 26, 2012.

Aartsma-Rus et al. "Theoretic Applicability of Antisense-Mediated Exon Skipping for Duchenne Muscular Dystrophy" *Human Mutation*. 2009 pp. 293-299 vol. 30 No. 3.

Alter et al., "Systemic delivery of morpholino oligonucleotide restores dystrophin expression bodywide and improves dystrophic pathology." *Nature Medicine*. Feb. 2006;12(2):175-7. Epub Jan. 29, 2006.

Barany "The ligase chain reaction in a PCR world." PCR Methods Appl. Aug. 1991;1(1):5-16.

Denny et al., "Oligo-riboprobes. Tools for in situ hybridisation". Histochemistry (1988) 89:481-493.

Fu et al., "An Unstable Triplet Repeat in a Gene Related to Myotonic Muscular Dystrophy", *Science*, vol. 255, 1256-1258. 1992.

Heemskerk et al. "Development of Antisense-Mediated Exon Skipping as a Treatment for Duchenne Muscular Dystrophy." *Ann NY Acad Sci*. vol. 1175 pp. 71-79. 2009.

Heemskerk et al. "Preclinical PK and PD Studies on 2' O-methyl-phosphorothioate RNA antisense Oligonucleotides in the MDX Mouse Model." *Mol Ther*. vol. 18(6) pp. 1210-1217. 2010.

Ito et al., "Purine-Rich Exon Sequences are not Necessarily Splicing Enhancer Sequence in the Dystrophin Gene." *Kobe J. Med. Sci*. 47, 193/202, Oct. 2001.

Kinali et al. "Local Restoration of Dystrophin Expression With the Morpholino Oligomer AVI-4658 in Duchenne Muscular Dystrophy: A Single-blind, Placebo-Controlled Dose-Escalation, Proof-of Concept Study." *Lancet Neurol*. vol. 8(10) pp. 918-928. 2009.

Politano et al., "Gentamicin administration in Duchenne patients with Premature stop codon. Preliminary results." *Acta Myologica* 22:15-21, 2003.

Popplewell et al. "Design of Phosphorodiamidate Morpholino Oligomers (PMOs) for the Induction of Exon Skipping of the Human DMD Gene." *Mol. Ther* vol. 17(3) pp. 554-561. 2009.

Reitter B. "Deflazacort vs. prednisone in Duchenne muscular dystrophy: trends of an ongoing study." Brain Dev. 1995;17 Suppl:39-43.

Smith et al., "Muscle-specific peptide #5", Mar. 23, 1999. From http://www.ebi.ac.uk/cgi-bin/epo/epofetch?AAW89659, downloaded Jul. 16, 2007. XP 002442550.

Spitali et al. "Exon skipping mediated dystrophin reading frame restoration for small mutations." *Hum Mut.* vol. 30(11) pp. 1527-1534. 2009.

Van Vliet et al., "Assessment of the feasibility of exon 45-55 multiexon skipping for duchenne muscular dystrophy." *BMC Medical Genetics*, Dec. 2008, vol. 9:105 (7 pages).

Wang et al. "Adeno-associated virus vector carrying human minidystrophin genes effectively ameliorates muscular dystrophy in mdx mouse model", Dec. 5, 2000, *P.N.A.S.* 97(25):13714-13719.

\* cited by examiner

GM00305 cells (HD)

METHODS AND MEANS FOR TREATING DNA REPEAT INSTABILITY ASSOCIATED GENETIC DISORDERS

RELATED APPLICATIONS

This application is a Continuation of PCT Application No. PCT/NL2009/050049, filed Feb. 5, 2009, which claims priority to European Patent Application No. 08151228.7, filed Feb. 8, 2008. The contents of each is incorporated by reference herein.

FIELD OF THE INVENTION

The current invention relates to the field of medicine, in particular to the treatment of genetic disorders associated with genes that have unstable repeats in their coding or non-coding sequences, most in particular unstable repeats in the human Huntington disease causing HD gene or the myotonic dystrophy type 1 causing DMPK gene.

BACKGROUND OF THE INVENTION

Instability of gene-specific microsatellite and minisatellite repetitive sequences, leading to increase in length of the repetitive sequences in the satellite, is associated with about 35 human genetic disorders. Instability of trinucleotide repeats is for instance found in genes causing X-linked spinal and bulbar muscular atrophy (SBMA), myotonic dystrophy type 1 (DM1), fragile X syndrome (FRAX genes A, E, F), Huntington's disease (HD) and several spinocerebellar ataxias (SCA gene family). Unstable repeats are found in coding regions of genes, such as the Huntington's disease gene, whereby the phenotype of the disorder is brought about by alteration of protein function and/or protein folding. Unstable repeat units are also found in untranslated regions, such as in myotonic dystrophy type 1 (DM1) in the 3' UTR or in intronic sequences such as in myotonic dystrophy type 2 (DM2). The normal number of repeats is around 5 to 37 for DMPK, but increases to premutation and full disease state two to ten fold or more, to 50, 100 and sometimes 1000 or more repeat units. For DM2/ZNF9 increases to 10,000 or more repeats have been reported. (Cleary and Pearson, Cytogenet. Genome Res. 100: 25-55, 2003).

The causative gene for Huntington's disease, HD, is located on chromosome 4. Huntington's disease is inherited in an autosomal dominant fashion. When the gene has more than 35 CAG trinucleotide repeats coding for a polyglutamine stretch, the number of repeats can expand in successive generations. Because of the progressive increase in length of the repeats, the disease tends to increase in severity and presents at an earlier age in successive generations, a process called anticipation. The product of the HD gene is the 348 kDa cytoplasmic protein huntingtin. Huntingtin has a characteristic sequence of fewer than 40 glutamine amino acid residues in the normal form; the mutated huntingtin causing the disease has more than 40 residues. The continuous expression of mutant huntingtin molecules in neuronal cells results in the formation of large protein deposits which eventually give rise to cell death, especially in the frontal lobes and the basal ganglia (mainly in the caudate nucleus). The severity of the disease is generally proportional to the number of extra residues.

DM1 is the most common muscular dystrophy in adults and is an inherited, progressive, degenerative, multisystemic disorder of predominantly skeletal muscle, heart and brain. DM1 is caused by expansion of an unstable trinucleotide (CTG)n repeat in the 3' untranslated region of the DMPK gene (myotonic dystrophy protein kinase) on human chromosome 19q (Brook et al, Cell, 1992). Type 2 myotonic dystrophy (DM2) is caused by a CCTG expansion in intron 1 of the ZNF9 gene, (Liguori et al, Science 2001). In the case of myotonic dystrophy type 1, the nuclear-cytoplasmic export of DMPK transcripts is blocked by the increased length of the repeats, which form hairpin-like secondary structures that accumulate in nuclear foci. DMPK transcripts bearing a long (CUG)n tract can form hairpin-like structures that bind proteins of the muscleblind family and subsequently aggregate in ribonuclear foci in the nucleus. These nuclear inclusions are thought to sequester muscleblind proteins, and potentially other factors, which then become limiting to the cell. In DM2, accumulation of ZNF9 RNA carrying the (CCUG)n expanded repeat form similar foci. Since muscleblind proteins are splicing factors, their depletion results in a dramatic rearrangement in splicing of other transcripts. Transcripts of many genes consequently become aberrantly spliced, for instance by inclusion of fetal exons, or exclusion of exons, resulting in non-functional proteins and impaired cell function.

The observations and new insights above have led to the understanding that unstable repeat diseases, such as myotonic dystrophy type 1, Huntington's disease and others can be treated by removing, either fully or at least in part, the aberrant transcript that causes the disease. For DM1, the aberrant transcript that accumulates in the nucleus could be down regulated or fully removed. Even relatively small reductions of the aberrant transcript could release substantial and possibly sufficient amounts of sequestered cellular factors and thereby help to restore normal RNA processing and cellular metabolism for DM (Kanadia et al., PNAS 2006). In the case of HD, a reduction in the accumulation of huntingtin protein deposits in the cells of an HD patient can ameliorate the symptoms of the disease.

A few attempts have been made to design methods of treatment and medicaments for unstable repeat disease myotonic dystrophy type 1 using antisense nucleic acids, RNA interference or ribozymes.

(i) Langlois et al. (Molecular Therapy, Vol. 7 No. 5, 2003) designed a ribozyme capable of cleaving DMPK mRNA. The hammerhead ribozyme is provided with a stretch RNA complementary to the 3' UTR of DMPK just before the CUG repeat. In vivo, vector transcribed ribozyme was capable of cleaving and diminishing in transfected cells both the expanded CUG repeat containing mRNA as well as the normal mRNA species with 63 and 50% respectively. Hence, also the normal transcript is gravely affected by this approach and the affected mRNA species with expanded repeats are not specifically targeted.

(ii) Another approach was taken by Langlois et al., (Journal Biological Chemistry, vol 280, no. 17, 2005) using RNA interference. A lentivirus-delivered short-hairpin RNA (shRNA) was introduced in DM1 myoblasts and demonstrated to down regulate nuclear retained mutant DMPK mRNAs. Four shRNA molecules were tested, two were complementary against coding regions of DMPK, one against a unique sequence in the 3' UTR and one negative control with an irrelevant sequence. The first two shRNAs were capable of down regulating the mutant DMPK transcript with the amplified repeat to about 50%, but even more effective in down regulating the cytoplasmic wildtype transcript to about 30% or less. Equivalent synthetic siRNA delivered by cationic lipids was ineffective. The shRNA directed at the 3' UTR sequence proved to be ineffective for both transcripts. Hence, also this approach is not targeted selectively to the expanded repeat mRNA species.

(iii) A third approach by Furling et al. (Gene Therapy, Vol. 10, p 795-802, 2003) used a recombinant retrovirus expressing a 149-bp long antisense RNA to inhibit DMPK mRNA levels in human DM1 myoblasts. A retrovirus was designed to provide DM1 cells with the 149 bp long antisense RNA complementary to a 39 bp-long (CUG)13 repeat and a 110 bp region following the repeat to increase specificity. This method yielded a decrease in mutated (repeat expanded) DMPK transcript of 80%, compared to a 50% reduction in the wild type DMPK transcript and restoration of differentiation and functional characteristics in infected DM1 myoblasts. Hence, also this approach is not targeted selectively to the expanded repeat mRNA species, it depends on a very long antisense RNA and can only be used in combination with recombinant viral delivery techniques.

DETAILED DESCRIPTION OF THE INVENTION

The methods and techniques described above provide nucleid acid based methods that cause non-selective breakdown of both the affected repeat expanded allele and unaffected or normal allele for genetic diseases that are associated with repeat instability and/or expansion. Moreover, the art employs sequences specific for the gene associated with the disease and does not provide a method that is applicable to several genetic disorders associated with repeat expansion. Finally, the art only teaches methods that involve use of recombinant DNA vector delivery systems, which need to be adapted for each oligonucleotide and target cell and which still need to be further optimised.

The current invention provides a solution for these problems by using a short nucleic acid molecule or oligonucleotide comprising or containing an inosine and/or uracile and/or a nucleotide containing a base able to form a wobble base pair, said nucleic acid molecule comprising or consisting of a sequence, which is complementary to the expanded repeat region only, i.e. it does not rely on hybridisation to unique sequences in exons or introns of the repeat containing gene. A second solution consists in using a short nucleic acid molecule that comprises or consists of a sequence, which is complementary to the expanded repeat region only and that is substantially not able to recruit and/or activate RNAse H; i.e. a RNAse H substantially independent nucleic acid molecule. Both solutions may also be combined: the invention provides the use of an oligonucleotide or nucleic acid molecule comprising an inosine and/or an uracile and/or a nucleotide containing a base able to form a wobble base pair, said oligonucleotide being substantially not able to recruit and/or activate RNAse H.

Without wishing to be bound by theory, the current invention may cause a decrease in transcript levels by alterations in posttranscriptional processing and/or splicing of the premature RNA. A decrease in transcript levels via alternative splicing and/or posttranscriptional processing may result in transcripts lacking the overly expanded or instable (tri)nucleotide repeat, but still possessing functional activities. In addition or alternatively, the stability of the mRNA may be decreased by the initiation or activation of breakdown mechanisms after binding to the target sequence in the mRNA. The reduction of aberrant transcripts by altered RNA processing and/or splicing and/or RNA stability may prevent accumulation and/or translation of aberrant, repeat expanded transcripts in cells.

Without wishing to be bound by theory the method of the current invention is also thought to provide specificity for the affected transcript with the expanded repeat because the kinetics for hybridisation to the expanded repeat are more favourable. The likelihood that a repeat specific complementary nucleic acid oligonucleotide molecule will hybridise to a complementary stretch in an RNA or DNA molecule increases with the size of the repetitive stretch. RNA molecules and in particular RNA molecules comprising repetitive sequences are normally internally paired, forming a secondary structure comprising open loops and closed hairpin parts. Only the open parts are relatively accessible for complementary nucleic acids. The short repeat stretches of a wild type transcript not associated with disease is often only 5 to about 20-40 repeats and due to the secondary structure relatively inaccessible for base pairing with a complementary nucleic acid. In contrast, the repeat units of the expanded repeat and disease associated allele is normally at least 2 fold expanded but usually even more, 3, 5, 10 fold, up to 100 or even more than 1000 fold expansion for some unstable repeat disorders. This expansion increases the likelihood that part of the repeat is, at least temporarily, in an open loop structure and thereby more accessible to base pairing with a complementary nucleic acid molecule, relative to the wild type allele. So despite the fact that the oligonucleotide is complementary to a repeat sequence present in both wild type and repeat-expanded transcripts and could theoretically hybridise to both transcripts, the current invention teaches that oligonucleotides complementary to a repetitive tract preferably hybridise to the disease-associated or disease-causing transcripts and leave the function of normal transcripts relatively unaffected. This selectivity is beneficial for treating diseases associated with repeat instability irrespective of the mechanism of reduction of the aberrant transcript. In addition, the 2 fold expanded but usually even more, 3, 5, 10 fold, up to 100 or even more than 1000 fold expansion allows for binding of more oligonucleotides, which may have additive effect on the mechanisms by which mutant transcripts are decreased. In the context of the invention, an oligonucleotide as designed herein is able to reduce "the repeat containing gene transcription" and/or to "treat any unstable cis-element DNA repeat associated genetic disorder" in a cell of a patient, in a tissue of a patient and/or in a patient. It preferably means that it reduces the detectable amount of disease-associated or disease-causing or mutant transcript containing an extending or unstable number of repetitive repeats in a cell of said patient, in a tissue of said patient and/or in a patient. Alternatively or in combination with previous sentence, said oligonucleotide may reduce the translation of said mutant transcript.

The invention thus provides a method for the treatment of unstable cis-element DNA repeat associated genetic disorders, by providing a nucleic acid molecule that is complementary to and/or capable of hybridising to the repetitive sequences only. This method thereby preferentially targets the expanded repeat transcripts and leaves the transcripts of the normal, wild type allele relatively unaffected. This is advantageous since the normal allele can thereby provide for the normal function of the gene, which is at least desirable and, depending on the particular gene with unstable DNA repeats, may in many cases be essential for the cell and/or individual to be treated. Therefore in the context of the invention, an oligonucleotide as designed herein can be used to treat any "cis-element repeat instability associated genetic disorder". Said disorder is preferably any disease wherein an allele of a given gene comprises a repetitive sequence which is a so-called unstable repetitive sequence, since the number of repeats present in said repetitive sequence will increase or expand in time during the development of said disease. Said increase or expand of the number of repeats occurs in one given individual and/or in successive generations (off-spring) of a given individual.

Furthermore, this approach is not limited to a particular unstable DNA repeat associated genetic disorder, but may be applied to any of the known unstable DNA repeat diseases, such as, but not limited to: coding regions repeat diseases having a polyglutamine (CAG) repeat: Huntington's disease, Haw River syndrome, Kennedy's disease/spinobulbar muscular atrophy, spino-cerebellar ataxia, or diseases having polyalanine (GCG) repeats such as: infantile spasm syndrome, deidocranial dysplasia, blepharophimosis/ptosis/epicanthus invensus syndrome, hand-foot-genital syndrome, synpolydactyl), oculopharyngeal muscular dystrophy, holoprosencephaly. Diseases with repeats in non-coding regions of genes to be treated according to the invention comprise the trinucleotide repeat disorders (mostly CTG and/or CAG and/or CCTG repeats): myotonic dystrophy type 1, myotonic dystrophy type 2, Friedreich's ataxia (mainly GAA), spinocerebellar ataxia, autism. Furthermore, a method of the invention can be applied to fragile site associated repeat disorder comprising various fragile X-syndromes, Jacobsen syndrome and other unstable repetitive element disorders such as myoclonus epilepsy, facioscapulohumeral dystrophy and certain forms of diabetes mellitus type 2.

Another advantage of the current invention is that an oligonucleotide specific for a repeat region may be administered directly to a cell and it does not rely on a vector-based delivery system. The techniques described in the prior art, for instance those mentioned above for treatment of DM1 and removal of DMPK transcripts from cells, require the use of vector based delivery systems to administer sufficient levels of oligonucleotides to the cell. The use of plasmid or viral vectors is yet less desirable for therapeutic purposes because of current strict safety regulations for therapeutic recombinant DNA vectors, the production of sufficient recombinant vectors for broad clinical application and the limited control and reversibility of an exaggerated (or non-specific) response after application. Nevertheless, optimisation in future is likely in these areas and viral delivery of plasmids could yield an advantageous long lasting effect. The current inventors have surprisingly found that an oligonucleotide comprising an inosine and/or an uracile and/or a nucleotide containing a base able to form a wobble base pair, said oligonucleotide comprising or consisting of a sequence that is complementary to repetitive sequences of expanded repeat transcripts, due to the expansion of their molecular target for hybridisation, has a much increased affinity and/or avidity for its target in comparison to an oligonucleotide that is specific for a unique sequence in a transcript. Because of this high affinity and avidity for the repeat expanded target transcript, lower amounts of said oligonucleotide suffice to yield sufficient inhibition and/or reduction of the repeat expanded allele by RNase H degradation, RNA interference degradation or altered post-transcriptional processing (comprising but not limited to splicing or exon skipping) activities. An oligonucleotide comprising an inosine and/or an uracile and/or a nucleotide containing a base able to form a wobble base pair, said oligonucleotide being complementary to repetitive sequences only, may be produced synthetically and is potent enough to be effective when delivered directly to a cell using commonly applied techniques for direct delivery of oligonucleotides to cells and/or tissues. Recombinant vector delivery systems may, when desired, be circumvented by using a method and an oligonucleotide of the current invention. The use of an oligonucleotide comprising an inosine and/or an uracile and/or a nucleotide containing a base able to form a wobble base pair is very attractive as explained below. Inosine for example is a known modified base, which can pair with three bases: uracil, adenine, and cytosine. Inosine is a nucleoside that is formed when hypoxanthine is attached to a ribose ring (also known as a ribofuranose) via a β-N-9-glycosidic bond. Inosine is commonly found in tRNAs and is essential for proper translation of the genetic code in wobble base pairs. A wobble base pair is a G-U and I-U/I-A/I-C pair fundamental in RNA secondary structure. Its thermodynamic stability is comparable to that of the Watson-Crick base pair. Wobble base pairs are critical for the proper translation of the genetic code. The genetic code makes up for disparities in the number of amino acids (20) for triplet codons (64), by using modified base pairs in the first base of the anti-codon. Similarly, when designing primers for polymerase chain reaction, inosine is useful in that it will indiscriminately pair with adenine, thymine, or cytosine. This allows one to design a primer that spans a single nucleotide polymorphism, without worry that the polymorphism will disrupt the primer's annealing efficiency. In the present invention, an inosine and/or an uracile and/or a nucleotide containing a base able to form a wobble base pair as present in an oligonucleotide as defined herein is preferably present in the part of said oligonucleotide which is complementary to a repetitive sequence as defined herein. However, an inosine and/or an uracile and/or a nucleotide containing a base able to form a wobble base pair may also be present in a part of said oligonucleotide which is not complementary to a repetitive sequence, for example in a targeting ligand as later identified herein.

In the current invention, expression of (triplet) nucleotide repeat expansion in mRNA can result in various diseases dependent on the triplet nucleotide repeat sequence and the gene involved. For instance, DM1 is caused by a (CUG)n repeat in exon 15 from the DMPK transcript, while HD is caused by a (CAG)n repeat in exon 1 from the huntingtin transcript. Specifically targeting these expansion repeats would require two oligonucleotides, however, employing an oligonucleotide comprising an inosine can lead to the design of one single oligonucleotide that is active against both transcripts, i.e. comprising or consisting of (CIG)n, (IGC)n or (GCI)n, preferably with a total nucleotide length between 9 and 50, more preferably between 12 and 40, most preferably between 15 and 30. Within the context of the whole application, the skilled person will understand that n is an integer which is preferably 1, 2, 3, 4, 5, 6, 7, 8, 9, 10, 11, 12, 13, 14, 15, 16, 17, 18, 19, 20 or more. However, the length of said oligonucleotide is not per se a multiple of 3. In an embodiment, an oligonucleotide of the invention has a length which is a multiple of 3. Therefore, using an inosine and/or an uracile and/or a nucleotide containing a base able to form a wobble base pair may lead to a reduction in the number of nucleic acid molecules that have to be designed and developed, for being potentially used as a medicament against several diseases. Table 2 illustrates how to design an oligonucleotide comprising an inosine and/or an uracile against each of the known repeats.

In a first aspect, the current invention discloses and teaches the use of an oligonucleotide, preferably comprising an inosine and/or an uracile and/or a nucleotide containing a base able to form a wobble base pair, said oligonucleotide being preferably substantially RNAse H independent and said oligonucleotide comprising or consisting of a sequence that is complementary only to a repetitive sequence in a human gene transcript for the manufacture of a medicament for the diagnosis, treatment or prevention of a cis-element repeat instability associated genetic disorders in humans. The invention hence provides a method of treatment for cis-element repeat instability associated genetic disorders.

In a second aspect, the invention also pertains to an oligonucleotide, preferably comprising an inosine and/or an uracile and/or a nucleotide containing a base able to form a wobble base pair, said oligonucleotide being preferably substantially RNAse H independent and said oligonucleotide being preferably used in the first aspect of the invention and/or applied in method of the invention to prevent the accumulation and/or translation of repeat expanded transcripts in cells.

An oligonucleotide preferably comprising an inosine and/or an uracile and/or a nucleotide containing a base able to form a wobble base pair is preferably RNAse H substantially independent and may comprise a sequence that is complementary only to a repetitive sequence as defined below. It means that said oligonucleotide may further comprise an additional part which is not complementary to a sequence present in a cell to be treated. This additional part may for example been added during cloning procedures, and/or be a targeting part as later defined herein.

In an alternative embodiment, it may mean that a oligonucleotide may further comprise an additional part which is complementary to a sequence present in a cell to be treated. This additional part may for example be a sequence flanking the repetitive region. Or, this additional part may for example be a sequence not directly flanking the repetitive region. Or, this additional part may for example be a sequence not directly flanking the repetitive region and contain a functional motif (e.g., but not limited, to an ESE). Or, this additional part may for example be a sequence not directly flanking the repetitive region but in proximity because of the secondary or tertiary structure. Preferably, the repetitive sequence is at least 50% of the length of the oligonucleotide of the invention, more preferably at least 60%, even more preferably at least 70%, even more preferably at least 80%, even more preferably at least 90% or more. In a most preferred embodiment, the oligonucleotide of the invention consists of a sequence that is complementary only to a repetitive sequence as defined below. For example, an oligonucleotide may comprise a sequence that is complementary only to a repetitive sequence as defined below and a targeting part, which is later on called a targeting ligand.

A repeat or repetitive element or repetitive sequence or repetitive stretch is herein defined as a consecutive repetition of at least 3, 4, 5, 10, 100, 1000 or more, of a repetitive unit or repetitive nucleotide unit or repeat nucleotide unit comprising a trinucleotide repetitive unit, or alternatively a 4, 5 or 6 nucleotide repetitive unit, in a transcribed gene sequence in the genome of a subject, including a human subject.

An oligonucleotide of the invention preferably contains or comprises an inosine and/or an uracile and/or a nucleotide containing a base able to form a wobble base pair. More preferably said oligonucleotide comprises an inosine and/or an uracile. In the context of the invention, contains preferably means comprises. An oligonucleotide comprising an inosine and/or an uracile and/or a nucleotide containing a base able to form a wobble base pair may be defined as an oligonucleotide wherein at least one nucleotide has been substituted with an inosine and/or an uracile and/or a nucleotide containing a base able to form a wobble base pair. The skilled person knows how to test whether a nucleotide contains a base able to form a wobble base pair. Since for example inosine can form a base pair with uracil, adenine, and/or cytosine, it means that at least one nucleotide able to form a base pair with uracil, adenine and/or cytosine has been substituted with inosine. However, in order to safeguard specificity, the inosine containing oligonucleotide preferably comprises the substitution of at least one nucleotide able to form a base pair with uracil or adenine or cytosine. More preferably, all nucleotides able to form a base pair with uracil or adenine or cytosine are substituted with inosine. For example an inosine containing oligonucleotide complementary to a repetitive element (CAG)n or (CUG)n will comprise or consist of (CIG)n, or (IGC)n, or (GCI)n. Examples of inosine and/or uracil containing oligonucleotides complementary to (CAG)n, (CUG)n, (CGG)n, (GCG)n, (GAA)n, (GCC)n or (CCUG)n are presented in table 2. For convenience in this table n is taken as being 2. The skilled person will understand that for an oligonucleotide of the invention, n is an integer being preferably comprised between 3 and 17 as defined later herein. It is also obvious for the skilled person that a specific oligonucleotide can be designed by starting or finishing at any position in a given repeat sequence (or motif) without prejudice that one or the other resulting sequences could be more efficient. For example an inosine containing oligonucleotide complementary to a repetitive element (CAG)n or (CUG)n will comprise or consist of (CIG)n, or (IGC)n, or (GCI)n. It is also to be encompassed by the present invention that since at least one nucleotide has been substituted by inosine and/or uracile and/or a nucleotide containing a base able to form a wobble base pair in an oligonucleotide as defined herein, that an oligonucleotide complementary to a repetitive element such as (CAG)n may comprise or consist of (CIG)n. As indicated above, said complementary oligonucleotide may also comprise or consist of (IGC)n or (GCI)n. If one takes (CIG)n as example, having n as 3 as example, the invention encompasses any possible oligonucleotide based on a given formula such as (CIG)₃ comprising 1 or 2 or 3 inosine(s) at the indicated position: (CTG)(CIG)(CTG), (CIG)(CTG)(CTG), (CIG)(CTG)(CIG), (CIG)(CIG)(CTG), (CIG)(CIG)(CIG).

An oligonucleotide which comprises an inosine and/or an uracile and/or a nucleotide containing a base able to form a wobble base pair said oligonucleotide being preferably RNAse H substantially independent may be single stranded or double stranded. Double stranded means that the oligonucleotide is an heterodimer made of two complementary strands, such as in a siRNA. In a preferred embodiment, an oligonucleotide is single stranded. The skilled person will understand that it is however possible that a single stranded oligonucleotide may form an internal double stranded structure. However, this oligonucleotide is still named as a single stranded oligonucleotide in the context of this invention. A single stranded oligonucleotide has several advantages compared to a double stranded siRNA oligonucleotide: (i) its synthesis is expected to be easier than two complementary siRNA strands; (ii) there is a wider range of chemical modifications possible to optimise more effective uptake in cells, a better (physiological) stability and to decrease potential generic adverse effects; (iii) siRNAs have a higher potential for non-specific effects (including off-target genes) and exaggerated pharmacology (e.g. less control possible of effectiveness and selectivity by treatment schedule or dose) and (iv) siRNAs are less likely to act in the nucleus and cannot be directed against introns. Therefore, in a preferred embodiment of the first aspect, the invention relates to the use of a single stranded oligonucleotide preferably comprising an inosine and/or an uracile and/or a nucleotide containing a base able to form a wobble base pair, said oligonucleotide being preferably RNAse H substantially independent and said oligonucleotide comprising or consisting of a sequence that is complementary only to a repetitive sequence in a human gene transcript for the manufacture of a medicament for the diagnosis, treatment or prevention of a cis-element repeat instability associated genetic disorders in humans.

Said oligonucleotide preferably comprises at least 9 to about 50 consecutive nucleotides complementary to a repetitive element, or at least 9 to 50 consecutive nucleotides complementary to a repetitive element, more preferably 12 to 45 nucleotides, even more preferably 12 to 40 nucleotides, even more preferably 12 to 30, even more preferably 15 to 30 nucleotides and most preferably 12 to 25 nucleotides complementary to a repetitive stretch, preferably having a trinucleotide repeat unit or a tetranucleotide repeat unit. The oligonucleotide preferably comprising an inosine and/or an uracile and/or a nucleotide containing a base able to form a wobble base pair and being preferably RNAse H substantially independent may be complementary to and/or capable of hybridizing to a repetitive stretch in a coding region of a transcript, preferably a polyglutamine (CAG) or a polyalanine (GCG) coding tract. The oligonucleotide may also be complementary to and/or capable of hybridizing to a non-coding region for instance 5' or 3' untranslated regions, or intronic sequences present in precursor RNA molecules.

In a preferred embodiment, an oligonucleotide preferably comprising an inosine and/or an uracile and/or a nucleotide containing a base able to form a wobble base pair and being preferably RNAse H substantially independent and to be used in a method of the invention comprises or consists of a sequence that is complementary to a repetitive element having as repetitive nucleotide unit a repetitive nucleotide unit selected from the group consisting of (CAG)n (SEQ ID NO:16), (GCG)n (SEQ ID NO:10), (CUG)n (SEQ ID NO:17), (CGG)n (SEQ ID NO:11), (GAA)n (SEQ ID NO:13), (GCC)n (SEQ ID NO:14), and (CCUG)n (SEQ ID NO:15). Said oligonucleotide may be a single or double stranded oligonucleotide. In a preferred embodiment, the oligonucleotide is double stranded. Since a oligonucleotide preferably comprises at least 9 to about 50 consecutive nucleotides complementary to a repetitive element, more preferably comprises at least 9 to 50 consecutive nucleotides complementary to a repetitive element, it means n is an integer comprised between 3 and 17, more preferably between 4 and 15, even more preferably between 4 and 14, even more preferably between 4 and 13, even more preferably between 4 and 10, even more preferably between 5 and 10, and most preferably between 4 and 8 or between 4 and 9.

The use of an oligonucleotide preferably comprising an inosine and/or an uracile and/or a nucleotide containing a base able to form a wobble base pair, being preferably RNAse H substantially independent and comprising or consisting of a sequence that is complementary to a polyglutamine (CAG)n tract in a transcript is particularly useful for the diagnosis, treatment and/or prevention of the human disorders Huntington's disease, several forms of spino-cerebellar ataxia or Haw River syndrome, X-linked spinal and bulbar muscular atrophy and/or dentatorubral-pallidoluysian atrophy caused by repeat expansions in the HD, HDL2/JPH3, SBMA/AR, SCA1/ATX1, SCA2/ATX2, SCA3/ATX3, SCA6/CACNA1A, SCA7, SCA17, AR or DRPLA human genes. Such an oligonucleotide, preferably such an oligonucleotide comprising an inosine preferably comprises or consists of (CIG)n, or (IGC)n, or (GCI)n. For other preferred possibilities see table 2.

The use of an oligonucleotide preferably comprising an inosine and/or an uracile and/or a nucleotide containing a base able to form a wobble base pair, being preferably RNAse H substantially independent and comprising or consisting of a sequence that is complementary to a polyalanine (GCG)n tract in a transcript is particularly useful for the diagnosis, treatment and/or prevention of the human disorders: infantile spasm syndrome, deidocranial dysplasia, blepharophimosis, hand-foot-genital disease, synpolydactyl), oculopharyngeal muscular dystrophy and/or holoprosencephaly, which are caused by repeat expansions in the ARX, CBFA1, FOXL2, HOXA13, HOXD13, OPDM/PABP2, TCFBR1 or ZIC2 human genes. For preferred oligonucleotides, see table 2.

The use of an oligonucleotide preferably comprising an inosine and/or an uracile and/or a nucleotide containing a base able to form a wobble base pair being preferably RNAse H substantially independent and comprising or consisting of a sequence that is complementary to a (CUG)n repeat in a transcript and is particularly useful for the diagnosis, treatment and/or prevention of the human genetic disorder myotonic dystrophy type 1, spino-cerebrellar ataxia 8 and/or Huntington's disease-like 2 caused by repeat expansions in the DM1/DMPK, SCA8 or JPH3 genes respectively. Preferably, these genes are from human origin. Such an oligonucleotide, preferably such an inosine containing oligonucleotides preferably comprises or consists of (CIG)n, or (IGC)n, or (GCI)n. For other preferred oligonucleotides, see table 2.

The use of an oligonucleotide preferably comprising an inosine and/or an uracile and/or a nucleotide containing a base able to form a wobble base pair, being preferably RNAse H substantially independent and comprising or consisting of a sequence that is complementary to a (CCUG)n repeat in a transcript is particularly useful for the diagnosis, treatment and/or prevention of the human genetic disorder myotonic dystrophy type 2, caused by repeat expansions in the DM2/ZNF9 gene. For preferred oligonucleotides, see table 2.

The use of an oligonucleotide preferably comprising an inosine and/or an uracile and/or a nucleotide containing a base able to form a wobble base pair being preferably RNAse H substantially independent and comprising or consisting of a sequence that is complementary to a (CGG)n repeat in a transcript is particularly useful for the diagnosis, treatment and/or prevention of human fragile X syndromes, caused by repeat expansion in the FRAXA/FMR1, FRAXE/FMR2 and FRAXF/FAM11A genes. For preferred oligonucleotides see table 2.

The use of an oligonucleotide preferably comprising an inosine and/or an uracile and/or a nucleotide containing a base able to form a wobble base pair being preferably RNAse H substantially independent and comprising or consisting of a sequence that is complementary to a (CCG)n (SEQ ID NO:12) repeat in a transcript is particularly useful for the diagnosis, treatment and/or prevention of the human genetic disorder Jacobsen syndrome, caused by repeat expansion in the FRA11B/CBL2 gene. For preferred oligonucleotides, see table 2.

The use of an oligonucleotide preferably comprising an inosine and/or an uracile and/or a nucleotide containing a base able to form a wobble base pair being preferably RNAse H substantially independent and comprising or consisting of a sequence that is complementary to a (GAA)n repeat in a transcript is particularly useful for the diagnosis, treatment and/or prevention of the human genetic disorder Friedreich's ataxia. For preferred oligonucleotides, see table 2.

The use of an oligonucleotide preferably comprising an inosine and/or an uracile and/or a nucleotide containing a base able to form a wobble base pair being preferably RNAse H substantially independent and comprising or consisting of a sequence that is complementary to a (ATTCT)n repeat in an intron is particularly useful for the diagnosis, treatment and/or prevention of the human genetic disorder Spinocerebellar ataxia type 10 (SCA10). For preferred oligonucleotides, see table 2.

The repeat-complementary oligonucleotide or oligonucleotide to be used in a method of the invention may comprise or consist of RNA, DNA, Locked nucleic acid (LNA), peptide nucleic acid (PNA), morpholino phosphorodiamidates (PMO), ethylene bridged nucleic acid (ENA) or mixtures/hybrids thereof that comprise combinations of naturally occurring DNA and RNA nucleotides and synthetic, modified nucleotides. The skilled person will understand that any human nucleotide bases, but also any other natural or synthetic nucleotide bases or their derivatives can be used such as for instance: 2-aminopurine, thymidine instead of uracile, 5-methylcytosine, 5-methylinosine, 7-methylguanosine or diaminoadenine. A person skilled in the art will also recognize that there are many synthetic derivatives of oligonucleotides. Therefore, "Oligonucleotide" includes, but is not limited to phosphodiesters, phosphotriesters, phosphorothioates, phosphodithioates, phosphorothiodiamidate and H-phosphonates derivatives. It encompasses also both naturally occurring and synthetic oligonucleotide derivatives.

In such oligonucleotides, the phosphodiester backbone chemistry may further be replaced by other modifications, such as phosphorothioates or methylphosphonates. Other oligonucleotide modifications exist and new ones are likely to be developed and used in practice. However, all such oligonucleotides have the character of an oligomer with the ability of sequence specific binding to RNA. Therefore in a preferred embodiment, the oligonucleotide comprises or consists of RNA nucleotides, 2'O-substituted RNA nucleotides, DNA nucleotides, locked nucleic acid (LNA) nucleotides, peptide nucleic acid (PNA) nucleotides, morpholino phosphorodiamidates, ethylene-bridged nucleic acid (ENA) nucleotides or mixtures thereof with or without phosphorothioate containing backbones.

Oligonucleotides containing at least in part naturally occurring DNA nucleotides are useful for inducing degradation of DNA-RNA hybrid molecules in the cell by RNase H activity (EC.3.1.26.4).

Naturally occurring RNA ribonucleotides or RNA-like synthetic ribonucleotides comprising oligonucleotides may be applied in the method of the invention to form double stranded RNA-RNA hybrids that act as enzyme-dependent antisense through the RNA interference or silencing (RNAi/siRNA) pathways, involving target RNA recognition through sense-antisense strand pairing followed by target RNA degradation by the RNA-induced silencing complex (RISC).

Alternatively or in addition, steric blocking antisense oligonucleotides (RNase-H independent antisense) interfere with gene expression or other precursor RNA or messenger RNA-dependent cellular processes, in particular but not limited to RNA splicing and exon skipping, by binding to a target sequence of RNA transcript and getting in the way of processes such as translation or blocking of splice donor or splice acceptor sites. Alteration of splicing and exon skipping techniques using modified antisense oligonucleotides are well documented, known to the skilled artisan and may for instance be found in U.S. Pat. No. 6,210,892, WO9426887, WO04/083446 and WO02/24906. Moreover, steric hindrance may inhibit the binding of proteins, nuclear factors and others and thereby contribute to the decrease in nuclear accumulation or ribonuclear foci in diseases like DM1.

An oligonucleotide as defined herein, which may comprise synthetic or modified nucleotides, complementary to (expanded) repetitive sequences is useful in a method of the invention for reducing or inactivating repeat containing transcripts via the siRNA/RNA interference or silencing pathway.

Single or double stranded oligonucleotides to be used in a method of the invention may comprise or consist of DNA nucleotides, RNA nucleotides, 2'-O substituted ribonucleotides (preferably 2'-O-substituted RNA phosphorothioate nucleotides), including alkyl and methoxy ethyl substitutions (including 2'-4' constrained variants as identified herein), peptide nucleic acid (PNA), locked nucleic acid (LNA) and morpholino (PMO) antisense oligonucleotides and ethylene-bridged nucleotides (ENA) and combinations thereof, optionally chimeras with RNAse H dependent antisense. A preferred oligonucleotide comprises 2'-O-substituted RNA phosphorothioate nucleotides, preferably wherein the 2'-O-substitution is a methoxy ethyl (MOE) and/or methyl (Me) and/or 2'O,4'C methylene bridge (LNA) and/or 2'O, 4'C constrained ethyl (cEt) and/or 2'O, 4'C constrained methoxyethyl (cMOEt) (reference: Short Antisense Oligonucleotides with Novel 2'-4' Conformationaly Restricted Nucleoside Analogues Analogues Show Improved Potency without Increased Toxicity in Animals. Punit P. Seth, Andrew Siwkowski, Charles R. Allerson, Guillermo Vasquez, Sam Lee, Thazha P. Prakash, Edward V. Wancewicz, Donna Witchell, and Eric E. Swayze J. Med. Chem., 2009, 52 (1), 10-13). Integration of locked nucleic acids in the oligonucleotide changes the conformation of the helix after base pairing and increases the stability of the duplex. Integration of LNA bases into the oligonucleotide sequence can therefore be used to increase the ability of complementary oligonucleotides of the invention to be active in vitro and in vivo to increase RNA degradation inhibit accumulation of transcripts or increase exon skipping capabilities. Peptide nucleic acids (PNAs), an artificial DNA/RNA analog, in which the backbone is a pseudopeptide rather than a sugar, have the ability to form extremely stable complexes with complementary DNA oligomers, by increased binding and a higher melting temperature. Also PNAs are superior reagents in antisense and exon skipping applications of the invention. More preferably, an oligonucleotide to be used in a method of this invention comprises, at least in part or fully, 2'-O-methoxy ethyl phosphorothioate RNA nucleotides, 2'-O-methyl phosphorothioate RNA nucleotides and/or locked nucleic acids (LNA). Even more preferably, an oligonucleotide comprises or consists of LNA and 2'-O-methyl phosphorothioate RNA nucleotides. In another preferred embodiment, an oligonucleotide comprises or consists of LNA and phosphorothioate DNA nucleotides. In another preferred embodiment, an oligonucleotide comprises or consists of LNA and 2'-O-methyl phosphorothioate RNA nucleotides and phosphorothioate DNA nucleotides. In another preferred embodiment, an oligonucleotide comprises or consists of LNA and 2'-O-methoxy ethyl phosphorothioate RNA nucleotides. In another more preferred embodiment, an oligonucleotide consists of a PMO oligonucleotide. In another preferred embodiment, an oligonucleotide consists of 2'-O-methyl phosphorothioate RNA nucleotides. Most preferably these modifications will be employed in a configuration that will allow the breakdown or inhibition of mutant mRNA by other mechanisms than RNAse H. Oligonucleotides comprising or consisting of a sequence that is complementary to a repetitive sequence selected from the group consisting of (CAG)n, (GCG)n, (CUG)n, (CGG)n, (CCG)n, (GAA)n, (GCC)n and (CCUG)n having a length of 9 to 50, more preferably 12 to 40, most preferably 12 to 25 nucleotides, and comprising 2'-β-methoxyethyl phosphorothioate RNA nucleotides, 2'-O-methyl phosphorothioate RNA nucleotides, LNA nucleotides or PMO nucleotides are most preferred for use in the invention for the diagnosis, treatment of prevention of cis-element repeat instability genetic disorders.

Alternatively or in combination with one or more of the earlier defined preferred embodiments, the invention further specifically provides an oligonucleotide that comprises or consists of a sequence that is complementary only to a repetitive sequence in a gene transcript and its use for the manufacture of a medicament for the treatment or prevention of human cis-element repeat instability associated genetic disorders and which is a RNAse H susbtantially independent oligonucleotide.

A RNAse H substantially independent oligonucleotide is preferably defined as an oligonucleotide which is not able to substantially recruit and/or activate RNAse H after binding to a targeted RNA. The recruitment and/or activation of RNAse H may be assessed using a standard RNAse H digestion assay after having contacted a RNAse H, preferably from *E. coli*, a targeted RNA and an oligonucleotide to be tested. Such assay is known to the skilled person and may be carried out as described in Honcharenko D et al or Kurreck J et al (Honcharenko D et al, (2007), Biochemistry, 46:5635-5646, and Kurreck J et al (2002), Nucl. Ac. Res., 30:1911-1918). In the context of the invention, an oligonucleotide or a given dose or concentration of an oligonucleotide is preferably said not to be able to substantially recruit and/or activate RNAse H and/or said substantially RNAse H independent when in at least one of the two assays as defined above, less than 50% of a targeted RNA has been digested. More preferably, less than 45% of a targeted RNA has been digested, even more preferably less than 40%, 35%, 30%, 25%, 20%, 15%, 10%, 5% or less. Most preferably, an oligonucleotide or a given dose or concentration of said oligonucleotide is not able to recruit and/or activate RNAse H. In a preferred embodiment, it is expected that when an olignucleotide is used in a concentration range wherein said oligonucleotide acts as a medicament for said disease as identified herein, said oligonucleotide will not to be able to substantially recruit and/or activate RNAse H and/or will be said substantially RNAse H independent. In this case, in such assay, there is preferably no detection of a digestion of a targeted RNA. Such an oligonucleotide is a RNAse H independent oligonucleotide. Many forms of antisenses have been described so far including enzyme-dependent mechanisms to degrade target mRNA such as RNase H activity. RNAse H cleaves only in RNA-DNA duplexes and therefore in order to down regulate mRNA the antisense oligonucleotide should contain deoxyribose (DNA) nucleotides. Slight modifications such as the use of phosphorothioate deoxyribose nucleotides are allowed to retain this RNAse H activity. Chimeric oligonucleotides (or oligomers) have been used because of their stabilising properties (enhancing physiological stability or half life), such as the application of 2'O-alkyl and 2'O-methoxy ethyl modifications at the 3' and 5' end of the oligonucleotide. However, a stretch of deoxyribose nucleotides is still required for the recruitment of RNase H by the oligonucleotide-target RNA duplex. These chimeric oligonucleotides (with or without phosphorothioate backbone modifications) have been referred to as gapmers (see WO 2007/089611). It is believed that such (deoxyribose) gap should be preferably at least 6 nucleotides and more preferably 10 nucleotides long in order to be able to recruit and/or activate RNAse H.

Therefore, in a preferred embodiment of the invention, an oligonucleotide is designed that substantially does not recruit and/or activate RNAse H after binding to a targeted RNA. The present invention preferably employs oligonucleotides (oligomers) that are preferably susbtantially not able to recruit and/or activate RNAse H. Such oligonucleotides may comprise for instance 2'-O backbone modifications, preferably 2'O-alkyl or 2'O-methoxy ethyl, peptide nucleic acid (PNA), locked nucleic acid (LNA) or morpholino antisense. Such oligonucleotides could even be a chimeric molecule containing deoxy nucleotides, but with preferably less than 9 or most preferably with less than 6 deoxy nucleotides next to each other (consecutive deoxy nucleotide).

Surprisingly, the present invention demonstrates that a RNAse H substantially independent oligonucleotide can be used for the manufacture of a medicament for the treatment or prevention of human cis-element repeat instability associated genetic disorders. Said RNAse H substantially independent oligonucleotide is more attractive than a corresponding classical RNAse H dependent oligonucleotide since we can reasonably expect that such RNAse H substantially independent oligonucleotide is easier to be synthetised, is less toxic and more stabile than its corresponding RNAse H dependent counterpart.

Therefore, in a preferred embodiment, there is provided an oligonucleotide and its use, wherein the use is as earlier herein defined and wherein said oligonucleotide has a length of about 9 to about 50 nucleotides, is substituted at least one of its 5' or 3' ends and comprises less than 9, more preferably less than 6 consecutive deoxyriboses in the rest of its sequence. More preferred lengths of an oligonucleotide have already been defined herein. A preferred substitution includes a phosphorothioate containing backbone. A preferred phosphorothioate containing backbone includes 2'-O-substituted RNA phosphorothioate nucleotides. Preferred 2'-O-substituted RNA phosphorothioate nucleotides include 2'-O-substituted methoxy ethyl and/or methyl and/or 2'O,4'C methylene bridge (LNA) and/or 2'O, 4'C constrained ethyl (cEt) and/or 2'O, 4'C constrained methoxyethyl (cMOEt).

As herein defined, an oligonucleotide is substituted at least one of its 5' or 3' ends and comprises less than 9, more preferably less than 6 consecutive deoxyriboses in the rest of its sequence. The rest of the sequence is preferably the center of the sequence. An oligonucleotide substituted at both of its 5' or 3' ends as defined herein and comprising 9 or more consecutive deoxyriboses in the center of its sequence is called a gapmer. Gapmers have been extensively described in WO 2007/089611. Gapmers are designed to enable the recruitment and/or activation of RNAse H. Without wishing to be bound by theory, it is believed that RNAse H is recruited and/or activated via binding to the central region of the gapmer made of deoxyriboses. Oligonucleotides of the invention which are substantially independent of RNAse H are designed in order to have a central region which is susbtantially not able to recruit and/or activate RNAse H. In a preferred embodiment, the rest of the sequence of the oligonucleotide of the invention, more preferably its central part comprises less than 9, 8, 7, 6, 5, 4, 3, 2, 1, or no deoxyribose. Accordingly this oligonucleotide of the invention, is preferably partly till fully substituted as earlier defined herein. Partly substituted preferably means that the oligonucleotide comprises at least 50% of its nucleotides that have been substituted, at least 55%, 60%, 65%, 70%, 75%, 80%, 85%, 90%, 95%, or 100% (i.e. fully) substituted.

Accordingly, in a preferred embodiment, an oligonucleotide comprising an inosine and/or an uracile and/or a nucleotide containing a base able to form a wobble base pair, being preferably RNAse H susbstantially independent and being used in the invention comprises or consists of a sequence that is complementary to a repetitive sequence selected from the group consisting of (CAG)n, (GCG)n, (CUG)n, (CGG)n, (GAA)n, (GCC)n and (CCUG)n, has a length of 9 to 50 nucleotides and is further characterized by:
   a) comprising 2'-O-substituted RNA phosphorothioate nucleotides such as 2'-O-methyl or 2'-O-methoxy ethyl or 2'-O 4'C ethylene (cEt), 2'-O 4'C methoxyethylene (cMOE) RNA phosphorothiote nucleotides, LNA nucleotides, or PMO nucleotides. The nucleotides could be used in any combination and/or with DNA phosphorothioate or RNA nucleotides; and/or b) being a single stranded oligonucleotide.

Accordingly, in another preferred embodiment, an oligonucleotide comprising an inosine and/or an uracile and/or a nucleotide containing a base able to form a wobble base pair, being preferably RNAse H susbstantially independent and being used in the invention comprises or consists of a sequence that is complementary to a repetitive sequence selected from the group consisting of (CAG)n, (GCG)n, (CUG)n, (CGG)n, (GAA)n, (GCC)n and (CCUG)n, has a length of 9 to 50 nucleotides and is further characterized by:

a) comprising 2'-O-substituted RNA phosphorothioate nucleotides such as 2'-O-methyl or 2'-O-methoxy ethyl or 2'-O 4'C ethylene or 2'-O 4'C methoxyethylene RNA phosphorothioate nucleotides, LNA nucleotides, or PMO nucleotides. The nucleotides could be used in combination and/or with DNA phosphorothioate or RNA nucleotides; and/or b) being a double stranded oligonucleotide.

In a further preferred embodiment, the above preferred modifications will be employed in a configuration that will allow the breakdown of mutant mRNA by other mechanisms than RNAse H.

In case, the invention relates to a double stranded oligonucleotide with two complementary strands, the antisense strand, complementary only to a repetitive sequence in a human gene transcript, this double stranded oligonucleotide is preferably not the siRNA with antisense RNA strand (CUG) 7 (SEQ ID NO:18) and sense RNA strand (GCA)7 applied to cultured monkey fibroblast (COS-7) or human neuroblastoma (SH-SY5Y) cell lines with or without transfection with a human Huntington gene exon 1 fused to GFP and as depicted in Wanzhao Liu et al (Wanzhao Liu et al, (2003), Proc. Japan Acad, 79: 293-298). More preferably, the invention does neither relate to the double stranded oligonucleotide siRNA (with antisense strand (CUG) 7 (SEQ ID NO:18) and sense strand (GCA)7 (SEQ ID NO:19)) nor to its use for the manufacture of a medicament for the treatment or prevention of Huntington disease, even more preferably for the treatment or prevention of Huntington disease gene exon 1 containing construct.

Although use of a single oligonucleotide may be sufficient for reducing the amount of repeat expanded transcripts, such as nuclear accumulated DMPK or ZNF9 transcripts or segments thereof or sufficient reduction of accumulation of repeat expanded HD protein, it is also within the scope of the invention to combine 2, 3, 4, 5 or more oligonucleotides. An oligonucleotide comprising or consisting of a sequence that is complementary to a repetitive part of a transcript may be advantageously combined with another oligonucleotide that comprise or consist of sequences that are complementary to and/or capable of hybridizing with unique sequences in a repeat containing transcript. As earlier defined herein, the invention encompasses the use of an oligonucleotide containing an inosine and/or an uracile and/or a nucleotide containing a base able to form a wobble base pair and being preferably a RNAse H substantially independent oligonucleotide. It is also encompassed by the invention to combine the use of an oligonucleotide comprising an inosine and/or an uracile and/or a nucleotide containing a base able to form a wobble base pair containing oligonucleotide with another oligonucleotide being a RNAse H substantially independent oligonucleotide. The method of the invention and the medicaments of the invention comprising repeat specific oligonucleotides may also be combined with any other treatment or medicament for cis-element repeat instability genetic disorders. For diagnostic purposes the oligonucleotide comprising an inosine and/or an uracile and/or a nucleotide containing a base able to form a wobble base pair being preferably RNAse H substantially independent and being used in a method of the invention may be provided with a radioactive label or fluorescent label allowing detection of transcripts in samples, in cells in situ in vivo, ex vivo or in vitro. For myotonic dystrophy, labelled oligonucleotides may be used for diagnostic purposes, for visualisation of nuclear aggregates of DMPK or ZNF9 RNA transcript molecules with associated proteins. Fluorescent labels may comprise Cy3, Cy5, FITC, TRITC, Rhodamine, GFP and the like. Radioactive labels may comprise $^{3}$H, $^{35}$S, $^{32/33}$P, $^{125}$I. Enzymes and/or immunogenic haptens such as digoxigenin, biotin and other molecular tags (HA, Myc, FLAG, VSV, lexA) may also be used. Accordingly, in a further aspect, the invention discloses an vitro or ex vivo detection and/or diagnostic method wherein an oligonucleotide comprising aminosine and/or an uracile and/or a nucleotide containing a base able to form a wobble base pair being preferably RNAse H substantially independent as defined above is used.

The oligonucleotide comprising an inosine and/or an uracile and/or a nucleotide containing a base able to form a wobble base pair being preferably RNAse H substantially independent and being for use according to the invention is suitable for direct administration to a cell, tissue and/or organ in vivo of an individual affected by or at risk of developing a cis-element repeat instability disorder, and may be administered directly in vivo, ex vivo or in vitro. Alternatively, said oligonucleotide may be provided by a nucleic acid vector capable of conferring expression of said oligonucleotide in human cells, in order to allow a sustainable source of said oligonucleotides. Oligonucleotide molecules according to the invention may be provided to a cell, tissue, organ and/or subject to be treated in the form of an expression vector that is capable of conferring expression of the oligonucleotide in human cells. The vector is preferably introduced in a cell by a gene delivery vehicle. Preferred vehicles for delivery are viral vectors such as retroviral vectors, adeno-associated virus vectors (AAV), adenoviral vectors, Semliki Forest virus vectors (SFV), EBV vectors and the like. Also plasmids, artificial chromosomes, plasmids suitable for targeted homologous recombination and integration in the human genome of cells may be suitably applied for delivery of oligonucleotides. Preferred for the current invention are those vectors wherein transcription is driven from polIII promoters, and/or wherein transcripts are in the form fusions with U1 or U7 transcripts, which yield good results for delivering small transcripts.

In a preferred embodiment, a concentration of an oligonucleotide comprising an inosine and/or an uracile and/or a nucleotide containing a base able to form a wobble base pair being preferably RNAse H substantially independent is ranged between about 0.1 nM and about 1 µM is used. More preferably, the concentration used is ranged between about 0.3 to about 400 nM, even more preferably between about 1 to about 200 nM. Preferred concentrations are between 0.1 nM and 1 µM. More preferably, the concentration used is ranged between 0.3 to 400 nM, even more preferably between 1 to 200 nM. If several oligonucleotides are used, this concentration may refer to the total concentration of oligonucleotides or the concentration of each oligonucleotide added. The ranges of concentration of oligonucleotide(s) as given above are preferred concentrations for in vitro or ex vivo uses. The skilled person will understand that depending on the oligonucleotide(s) used, the target cell to be treated, the gene target and its expression levels, the medium used and the transfection and incubation conditions, the concentration of oligonucleotide(s) used may further vary and may need to be optimised any further.

More preferably, the oligonucleotide comprising an inosine and/or an uracile and/or a nucleotide containing a base able to form a wobble base pair, being preferably RNAse H substantially independent and used in the invention to prevent, treat or diagnose cis-element repeat instability disorders is synthetically produced and administered directly to a cell, a tissue, an organ and/or a patient or an individual or a subject in a formulated form in a pharmaceutically acceptable composition. The delivery of said pharmaceutical composition to the subject is preferably carried out by one or more parenteral injections, e.g. intravenous and/or subcutaneous and/or intramuscular and/or intrathecal and/or intraventricular administrations, preferably injections, at one or at multiple sites in the human body. An intrathecal or intraventricular administration (in the cerebrospinal fluid) is preferably realized by introducing a diffusion pump into the body of a subject. Several diffusion pumps are known to the skilled person.

Pharmaceutical compositions that are to be used to target an oligonucleotide molecules comprising or consisting of a sequence that is complementary to repetitive sequences as defined herein may comprise various excipients such as diluents, fillers, preservatives, solubilisers and the like, which may for instance be found in Remington: The Science and Practice of Pharmacy, 20th Edition. Baltimore, Md.: Lippincott Williams & Wilkins, 2000.

Particularly preferred for a method of the invention is the use of an excipient that will aid in delivery of said oligonucleotide to a cell and into a cell, in particular excipients capable of forming complexes, vesicles and/or liposomes that deliver substances and/or oligonucleotide(s) complexed or trapped in the vesicles or liposomes through a cell membrane. Many of these substances are known in the art. Suitable substances comprise polyethylenimine (PEI), ExGen 500, synthetic amphiphils (SAINT-18), Lipofectin™, DOTAP and/or viral capsid proteins that are capable of self assembly into particles that can deliver said oligonucleotide to a cell. Lipofectin represents an example of liposomal transfection agents. It consists of two lipid components, a cationic lipid N-[1-(2,3 dioleoyloxy)propyl]-N,N,N-trimethylammonium chloride (DOTMA) (cp. DOTAP which is the methylsulfate salt) and a neutral lipid dioleoylphosphatidylethanolamine (DOPE). The neutral component mediates the intracellular release. Another group of delivery systems are polymeric nanoparticles. Polycations such like diethylaminoethylaminoethyl (DEAE)-dextran, which are well known as DNA transfection reagent can be combined with butylcyanoacrylate (PBCA) and hexylcyanoacrylate (PHCA) to formulate cationic nanoparticles that can deliver oligonucleotides across cell membranes into cells. In addition to these common nanoparticle materials, the cationic peptide protamine offers an alternative approach to formulate oligonucleotides as colloids. This colloidal nanoparticle system can form so called proticles, which can be prepared by a simple self-assembly process to package and mediate intracellular release of an oligonucleotide as defined herein. The skilled person may select and adapt any of the above or other commercially available alternative excipients and delivery systems to package and deliver an oligonucleotide for use in the current invention to deliver such oligonucleotide for the treatment of cis-element repeat instability disorders in humans.

In addition, an oligonucleotide comprising an inosine and/or an uracile and/or a nucleotide containing a base able to form a wobble base pair being preferably RNAse H substantially independent could be covalently or non-covalently linked to a targeting ligand specifically designed to facilitate the uptake in to the cell, cytoplasm and/or its nucleus. Such ligand could comprise (i) a compound (including but not limited to a peptide(-like) structure) recognising cell, tissue or organ specific elements facilitating cellular uptake and/or (ii) a chemical compound able to facilitate the uptake in to a cell and/or the intracellular release of an oligonucleotide from vesicles, e.g. endosomes or lysosomes. Such targeting ligand would also encompass molecules facilitating the uptake of oligonucleotides into the brain through the blood brain barrier.

Therefore, in a preferred embodiment, an oligonucleotide comprising an inosine and/or an uracile and/or a nucleotide containing a base able to form a wobble base pair being preferably RNAse H substantially independent is part of a medicament or is considered as being a medicament and is provided with at least an excipient and/or a targeting ligand for delivery and/or a delivery device of said oligonucleotide to a cell and/or enhancing its intracellular delivery. Accordingly, the invention also encompasses a pharmaceutically acceptable composition comprising an oligonucleotide of the invention and further comprising at least one excipient and/or a targeting ligand for delivery and/or a delivery device of said oligonucleotide to a cell and/or enhancing its intracellular delivery.

The invention also pertains to a method for the reduction of repeat containing gene transcripts in a cell comprising the administration of a single strand or double stranded oligonucleotide comprising an inosine and/or an uracile and/or a nucleotide containing a base able to form a wobble base pair being preferably RNAse H substantially independent and preferably comprising 2'-O-substituted RNA phosphorothioate nucleotides such as 2'-O-methyl or 2'-O-methoxy ethyl RNA phosphorothioate nucleotides or LNA or cET or cMOE nucleotides or PMO nucleotides, and having a length of 9 to 50 nucleotides that are complementary to the repetitive sequence only. The nucleotides could be used in combination and/or with DNA phosphorothioate nucleotides.

In this document and in its claims, the verb "to comprise" and its conjugations is used in its non-limiting sense to mean that items following the word are included, but combinations and/or items not specifically mentioned are not excluded.

In addition the verb "to consist" may be replaced by "to consist essentially of" meaning that a molecule or a viral-based vector or a composition as defined herein may comprise additional component(s) than the ones specifically identified, said additional component(s) not altering the unique characteristic of the invention.

The word "about" or "approximately" when used in association with a numerical value (about 10) preferably means that the value may be the given value of 10 more or less 1% of the value.

In addition, reference to an element by the indefinite article "a" or "an" does not exclude the possibility that more than one of the element is present, unless the context clearly requires that there be one and only one of the elements. The indefinite article "a" or "an" thus usually means "at least one".

The present invention is further described by the following examples which should not be construed as limiting the scope of the invention.

FIGURE LEGENDS

FIG. 1: shows the concentration response curves in DM500 myotubes after treatment with various concentrations of oligonucleotide PS58 (SEQ ID NO:4) or PS142 (SEQ ID NO:5). Oligo(ribo)nucleotide PS58 (SEQ ID NO:4) exhibits a full length 2'O-methyl phosphorothioate modified backbone and oligo(deoxyribose)nucleotide PS 142 (SEQ ID NO:5) a full length phosphorothioate DNA backbone. The PS58 (SEQ ID NO:4) is more efficiently inhibiting mutant expanded hDMPK transcript than PS142 (SEQ ID NO:5). PS58 (SEQ ID NO:4), unlike PS142 (SEQ ID NO:5), contains the 2'OMe modification that prevents RNAse H mediated breakdown of target mRNA by oligonucleotides. The expression of hDMPK was quantified via Northern blot analysis followed by phosphoimager analysis. The signal was normalised to the GAPDH signal and expressed relative to the response after mock treatment.

Figure 2:
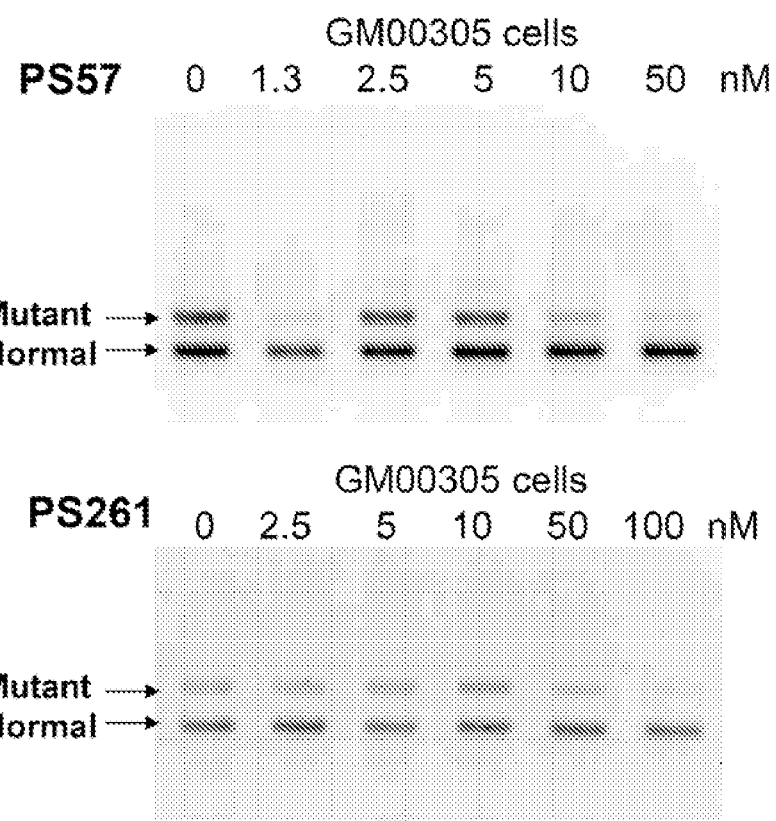

FIG. 2: RT-PCR analysis was performed on GM00305 fibroblasts from a male patient with Huntington's Disease after treatment with oligonucleotide PS57 (CUG)7 or PS261 (CIG)7 (SEQ ID NO:6) at various concentrations. Analysis of GM00305 shows two RT-PCR products representing the transcripts of both the mutant (expanded disease) allele and the normal allele. PS57 (SEQ ID NO:3) and PS261 (SEQ ID NO:6) show a dose dependent inhibition of the mutant transcript.

Figure 3:
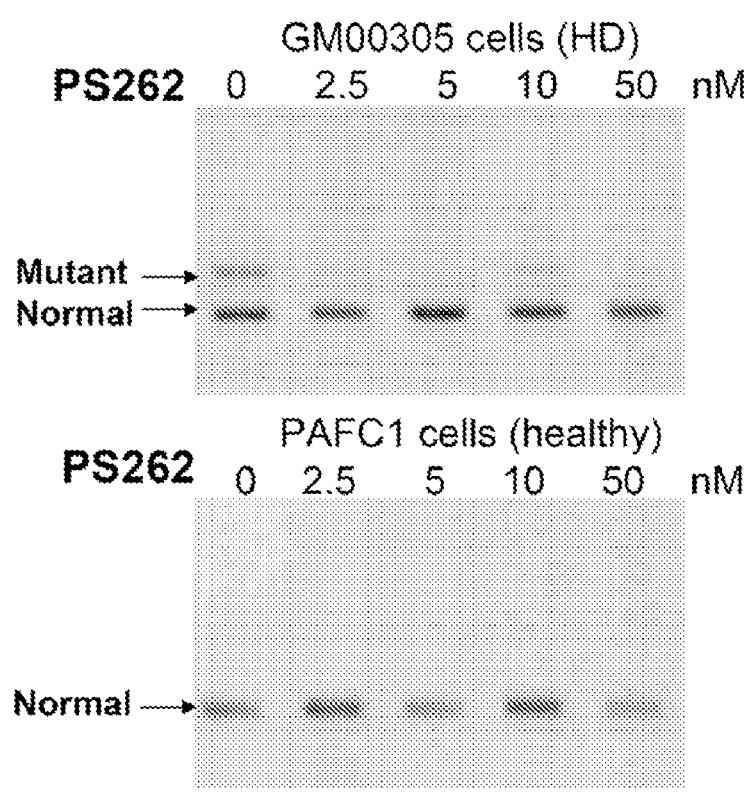

FIG. 3: RT-PCR analysis was performed on GM00305 fibroblasts from a male patient with Huntington's Disease or PAFC1 fibroblasts from a healthy volunteer after treatment with oligonucleotide PS262 (UGC)7 (SEQ ID NO:7) at various concentrations. Analysis of control treated GM00305 shows two RT-PCR products representing the transcripts of both the mutant (expanded disease) allele and the normal allele, while analysis of PAFC1 cells shows one RT-PCR products representing the transcripts of both normal alleles. PS262 (SEQ ID NO:7) shows a more efficient inhibition of the mutant transcript in GM00305 than the normal transcript in GM00305 or PAFC1.

Figure 4:
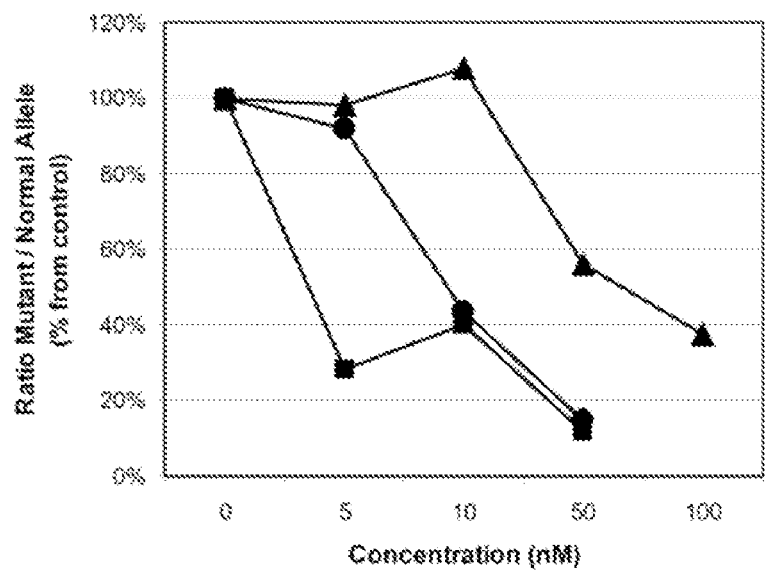

FIG. 4: The levels of RT-PCR products (from experiments also depicted in FIGS. 2 and 3) was determined for the mutant transcript as a ratio to the normal transcript and expressed as percentage of control treatment (which was set to 100%). The figure depicts concentration dependent decrease of the mutant-to-normal allele transcript in GM00305 cells after treatment with PS262 (SEQ ID NO:7) (squares), PS57 (SEQ ID NO:3) (circles) and PS261 (triangles) at different concentrations.

Figure 5:
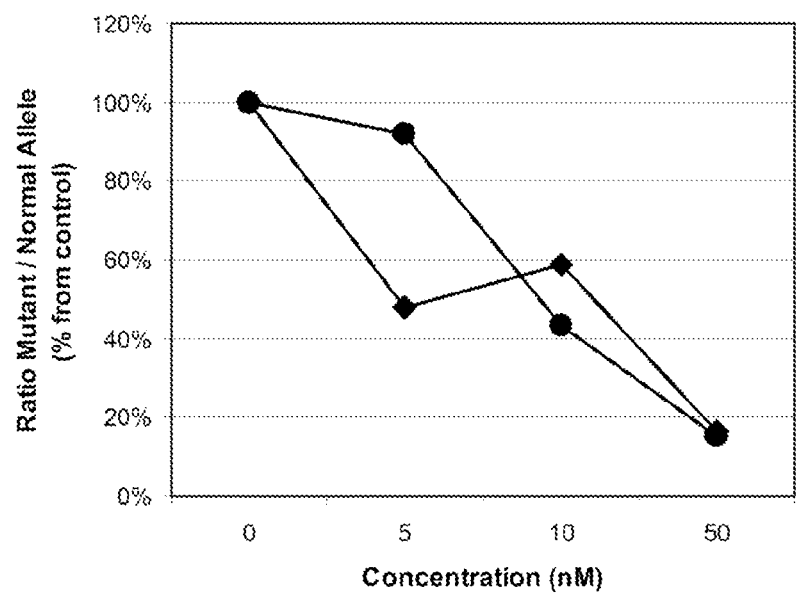

FIG. 5: RT-PCR analysis was performed on GM00305 fibroblasts from a male patient with Huntington's Disease after a 4 h treatment with oligonucleotide PS57(SEQ ID NO:3). Cells were harvested at 24 h (circles) or 48 h (diamonds) after the start of treatment. The levels of RT-PCR products was determined for the mutant transcript as a ratio to the normal transcript and expressed as percentage of control treatment (which was set to 100%). The figure depicts concentration dependent decrease of the mutant-to-normal allele transcript at 24 h (circles) or 48 h (diamonds) after the start of a 4 h treatment period with PS57 (SEQ ID NO:3).

Figure 6:
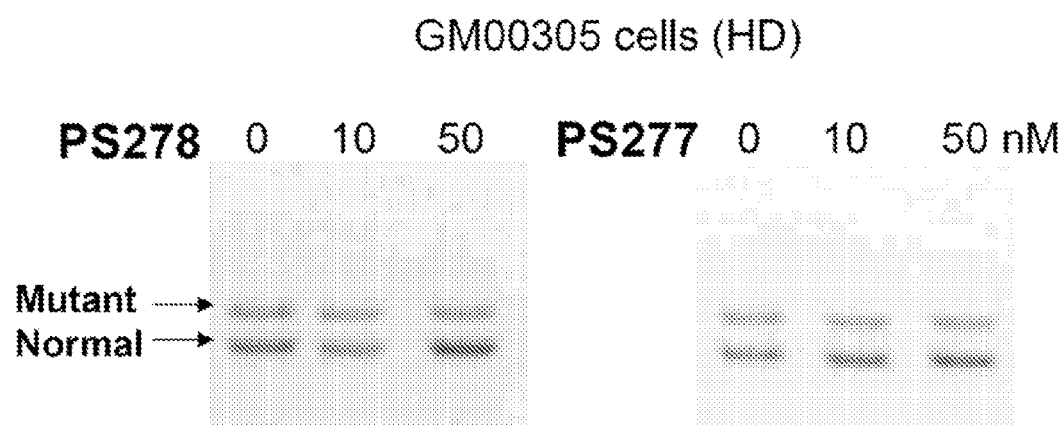

FIG. 6: RT-PCR analysis is presented from GM00305 fibroblast cells from a male patient with Huntington's Disease after treatment with oligonucleotide PS278 (SEQ ID NO:9) or PS277 (SEQ ID NO:8) or control. PS278 (SEQ ID NO:9) and PS277 (SEQ ID NO:8) are both gapmers (chimera's comprising 2'-O-methyl substitutions only on the 3' and 5' end of the oligonucleotides) in principle capable of activating RNAse H upon binding to target mRNA. PS277 (SEQ ID NO:8) contains a single mismatch. Analysis of GM00305 shows two RT-PCR products representing the transcripts derived from the mutant (expanded disease) allele and the normal allele.

Figure 7:
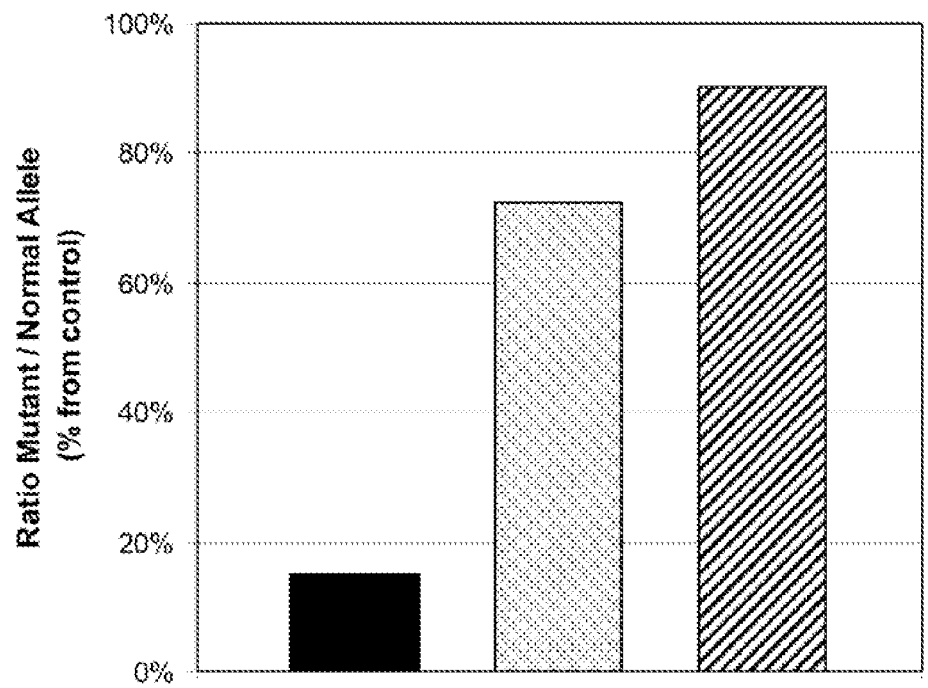

FIG. 7: The levels of RT-PCR products (from experiments also depicted in FIGS. 2 and 6) in GM00305 was determined for the mutant transcript as a ratio to the normal transcript and expressed as percentage of control treatment (which was set to 100%). The figure depicts concentration dependent decrease of the mutant-to-normal allele transcript after treatment with 50 nM of PS57 (SEQ ID NO:3) (closed), PS278 (SEQ ID NO:9) (stippled column) and PS261 (SEQ ID NO:6) (striped column).

Figure 8:
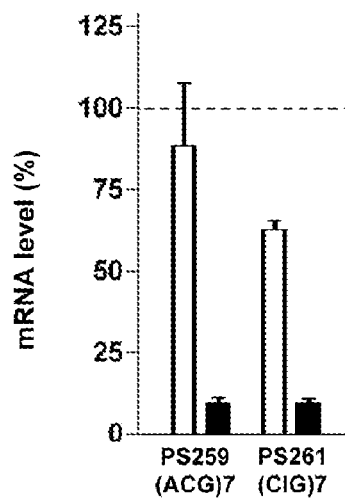

FIG. 8: shows the hDMPK mRNA levels (solid bars) in DM500 myotubes after treatment with 200 nM oligonucleotide PS259 (SEQ ID NO:20) (with an alternative starting nucleotide) or 200 nM oligonucleotide PS261 (SEQ ID NO:6) (comprising inosine (I) nucleotides instead of adenosine(A)). The expression of hDMPK was quantified via Northern blot analysis followed by phosphoimager analysis. The signal was normalised to the GAPDH signal and expressed relative to the response after mock treatment. Treatment with PS259 (SEQ ID NO:20) or PS261 (SEQ ID NO:6) resulted in decrease hDMPK mRNA levels. Solid bars depict hDMPK and open bars depict m (murine) DMPK; mDMPK does not contain a triplet nucleotide repeat region.

Figure 9:
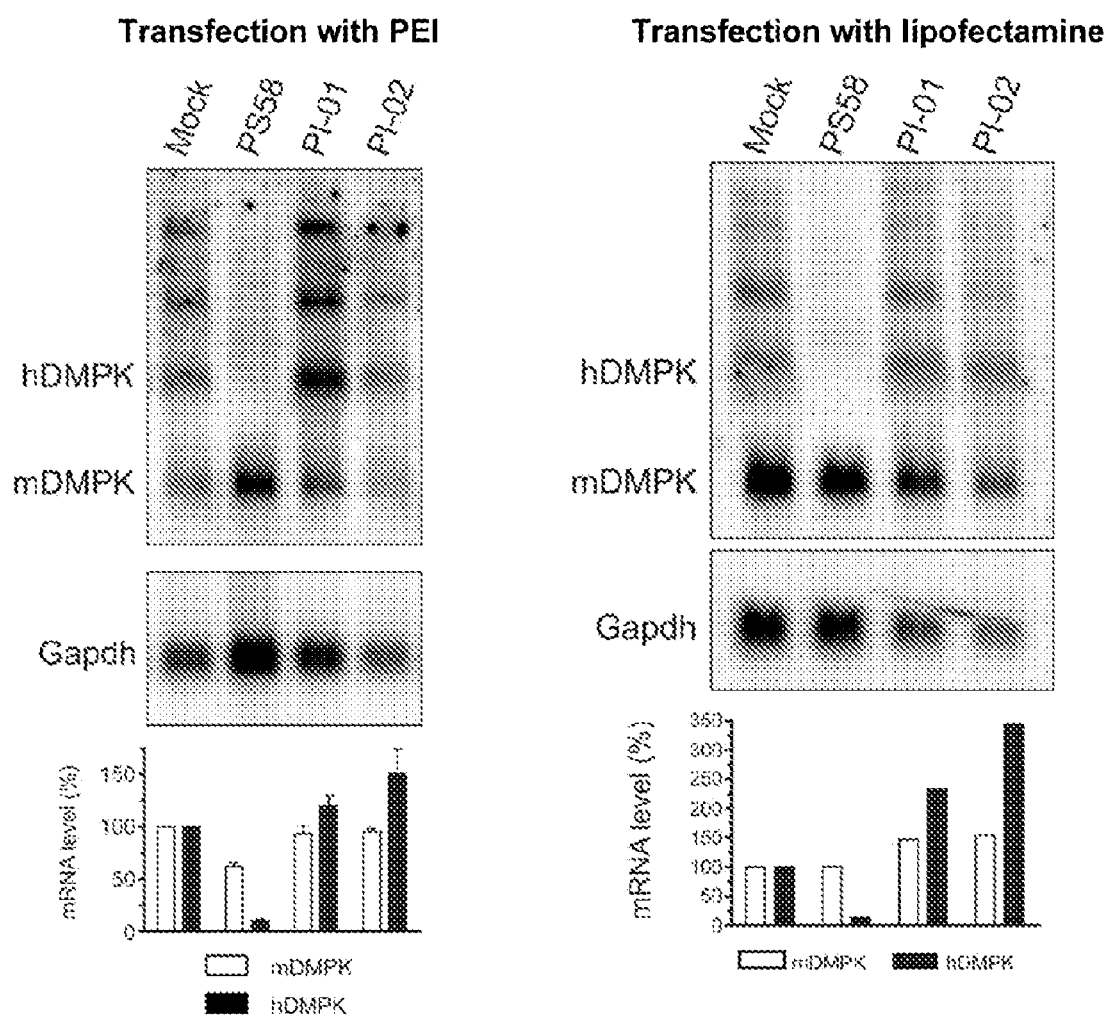

FIG. 9: shows the hDMPK mRNA levels in DM500 myotubes after treatment with double stranded siRNA oligonucleotide combinations PI-01 (SEQ ID NO:21 and SEQ ID NO:7) or PI-02 (SEQ ID NO:19 and SEQ ID NO:23) after transfection with PEI (200 nM oligonucleotide) or alternatively with lipofectamine 200° (50 nMoligonucleotide). The hDMPK signal after treatment has been depicted in FIG. 8 showing a lack of inhibition by the siRNA oligonucleotides compared to PS58 (SEQ ID NO:4). The expression of hDMPK was quantified via Northern blot analysis followed by phosphoimager analysis. The signal was normalised to the GAPDH signal and expressed relative to the response after mock treatment. Treatment with PI-01 (SEQ ID NO:21 and SEQ ID NO:7) or PI-02 (SEQ ID NO:19 and SEQ ID NO:23), both directed exclusively to the repetitive repeat sequence, did not resulted in a decrease hDMPK mRNA levels compared to effective oligonucleotide PS58 (SEQ ID NO:4).

EXAMPLES

Example 1

Immortomyoblast cell lines were derived from DM500 mice using standard techniques known to the skilled person. DM500 mice were derived from mice obtained from de Gourdon group in Paris. Immortomyoblast cell lines DM500 with variable (CTG)n repeat length of approximately 500 in the DMPK gene were grown subconfluent and maintained in a 5% $CO_2$ atmosphere at 33° C. on 0.1% gelatin coated dishes. Myoblast cells were grown subconfluent in DMEM supplemented with 20% FCS, 50 µg/ml gentamycin and 20 units of γ-interferon/ml. Myotube formation was induced by growing myoblast cells on Matrigel (BD Biosciences) coated dishes and placing a confluent myoblast culture at 37° C. and in DMEM supplemented with 5% horse serum and 50 µg/ml gentamycin. After five days on this low serum media contracting myotubes arose in culture and were transfected with the desired oligonucleotides. For transfection NaCl (500 mM, filter sterile), oligonucleotide and transfection reagens PEI (ExGen 500, Fermentas) were added in this specific order and directly mixed. The oligonucleotide transfection solution contained a ratio of 5 µl ExGen500 per ug oligonucleotide which is according to the instructions (ExGen 500, Fermentas). After 15 minutes of incubation at room temperature the oligonucleotide transfection solution was added to the low serum medium with the cultured myotubes and gently mixed. The final oligonucleotide concentration ranged from 10 μM to 600 nM. Mock control treatment is carried out with transfection solution without an oligonucleotide. After four hours of incubation at 37° C., fresh medium was added to the culture (resulting in a dilution of approximately 2.3×) and incubation was extended overnight at 37° C. The next day the medium containing the oligonucleotide was removed and fresh low serum medium was added to the myotubes which were kept in culture at 37° C. for another day. Fourty eight hours after the addition of oligonucleotide to the myotube culture (which is seven days after switching to low serum conditions to induced myotube formation), RNA was isolated with the "Total RNA mini kit" (Bio-Rad) and prepared for Northern blot and RT-PCR analysis. The Northern blot was hybridized with a radioactive human DMPK (hDMPK) probe and a mouse GAPDH probe. The probe used for DMPK is a human DMPK cDNA consisting of the DMPK open reading frame with full 3' UTR and 11 CTGs.

The human and mouse DMPK signal were quantified by phosphoimager analysis and normalized to the GAPDH signal.

FIG. 1 depicts the concentration dependent inhibition of the hDMPK signal of oligonucleotide PS58 (SEQ ID NO:4) and PS142 (SEQ ID NO:5). PS58 (SEQ ID NO:4), a fully modified 2'O-methyl phosphorothioate oligonucleotide unable to activate RNAse H after binding to the target mRNA, was effective at approximately 3000× fold lower concentration than the DNA phosphorothioate oligonucleotide PS142 (SEQ ID NO:5).

Example 2

Fibroblasts (GM 00305) from a male patient with Huntington's Disease were obtained from Coriell Cell Repository (Camden, N.J., US) and cultured according to the accompanying instructions and standard techniques known to the skilled person in the art. Huntington patients carry one healthy and one disease-causing allele of the Huntington gene resulting in the expression of both mRNAs with respectively a normal number and an expanded number of (CAG) repeats, respectively. Control fibroblasts (PAFC1) were obtained from a healthy volunteer with normal repeat length in both huntingtin alleles.

The fibroblasts were transfected with oligonucleotides PS57 (SEQ ID NO:3), PS261 (SEQ ID NO:6), PS262 (SEQ ID NO:7), PS277 (SEQ ID NO:8) and PS278 (SEQ ID NO:9), all directed to the complementary (CAG) triplet repeat in Huntingtin transcripts. A transfection was applied at several concentration levels using PEI as indicated by the manufacturer. Four hours after the start of treatment, the cells were washed and fresh medium was applied. Twenty four hours or eighty four hours after the start of transfection, the cells were harvested and total RNA was isolated and analysed by RT-PCR. Reversed transcription was carried out at 55° C. using random hexamers.

The Huntingtin transcript was determined using primers flanking the repeat expansion region in exon 1 (Forward: 5' ATGGCGACCCTGGAAAAGCTG 3' (SEQ ID NO:1) and 5' TGAGGCAGCAGCGGCTGT 3' (SEQ ID NO:2)). This method detects both types of Huntington mRNAs, the normal and also the mutant transcript with the additional (CAG) expansion which can be separately analyzed on a 2% agarose gels for qualitative evaluation or for quantification on the Agilent 2100 Bioanalyzer or Caliper LabChip90. The quantitative results for the RT-PCR product for the mutant transcript are expressed relative to those of for the normal transcript and expressed as percentage from the vehicle control treatment (without oligonucleotide) from the same patient fibroblasts (which was set to 100%).

The results of the experiments are depicted in FIGS. 2-7. FIGS. 1 to 3 show that three different oligonucleotides, (CUG)7 (SEQ ID NO:18), (UCG)7 (SEQ ID NO:7) or (CIG)7 (SEQ ID NO:6), which are all directed to specifically to the repeat sequence, can efficiently inhibit the mutant huntingtin transcripts with the expanded (CAG) repeat. These compounds are more effective against the mutant huntingtin transcript with a high number of disease causing (CAG) repeats than the normal transcript carrying a lower number of (CAG) repeats. This is demonstrated in the GM00305 cells derived from a Huntington patient, but also confirmed in a control cell from a healthy volunteer (PAFC1). The PCR products were confirmed by sequencing. FIG. 5 shows that the effect is not only present at 24 h after a 4 h treatment period but also after 48 h. This latter time point appears to be more optimal than 24 h as a clear inhibition starts already at a lower concentration. These results indicate that the effect will probably be maintained over a much longer period, despite a short 4 h treatment period.

Finally, FIGS. 7 and 8 depicts the results of two chimeric oligonucleotides. The nucleotides at the 3' and 5' end of the oligonucleotide have been modified with a 2'O-methyl substitution, but not the 10 nucleotides in the centre, resulting in a so-called gapmer. To a skilled person, a 2'O-methyl substitution (or the use of other modifications including 2'O-methoxy ethyl or locked nucleic acids) is known to limit RNAse H mediated breakdown after binding to the target mRNA. Such RNAse H mediated breakdown mechanism as a means of mRNA inhibition can be preserved by maintaining a stretch of (phosphorothioate) DNA nucleotides in the oligonucleotide ("the gap"). The results in FIGS. 7 and 8 however clearly indicate that the fully modified PS57 (SEQ ID NO:3) oligonucleotide is much more effective, effectively inhibiting the mutant HD transcript levels at the employed concentrations with equivocal or no inhibition by oligonucleotides PS278 (SEQ ID NO:9) or PS277 (SEQ ID NO:8).

Example 3

According to the methods described in example 1, myotubes derived from DM500 cells were treated with 200 nM oligonucleotide PS259 (SEQ ID NO:20) (with an alternative starting nucleotide compared to PS58 (SEQ ID NO:4)) or 200 nM oligonucleotide PS261 (SEQ ID NO:6) (comprising inosine (I) nucleotides instead of adenosine(A)). The hDMPK signal (solid bars) after treatment has been depicted in FIG. 8. demonstrating effective inhibition by the oligonucleotides.

Example 4

According to the methods described in example 1, myotubes derived from DM500 cells were treated with double stranded siRNA oligonucleotide combinations PI-01 (SEQ ID NO:21 and SEQ ID NO:7) or PI-02 (SEQ ID NO:19 and SEQ ID NO:23) after transfection with PEI (200 nM oligonucleotide) or alternatively with lipofectamine 200° (according to instructions of the manufacturer with 50 nM oligonucleotide). Oligonucleotide combinations (siRNA) PI-01 (SEQ ID NO:21 and SEQ ID NO:7) or PI-02 (SEQ ID NO:19 and SEQ ID NO:23) are complementary to the repetitive sequence only. The transfection protocol was performed twice during the treatment incubation period. The hDMPK signal after treatment has been depicted in FIG. 8 showing a lack of inhibition by the siRNA oligonucleotides compared to PS58 (SEQ ID NO:4).

TABLE 1

Overview oligonucleotides employed in the examples

| Oligo name | Backbone Modification | Sequence |
|---|---|---|
| PS57 | 2'OMe RNA phosphorothioate (with or without fluorescent FAM label) | CUGCUGCUGCUGCUGCUG (SEQ ID NO: 3) |
| PS58 | 2'OMe RNA phosphorothioate (with or without fluorescent FAM label) | CAGCAGCAGCAGCAGCAG (SEQ ID NO: 4) |
| PS142 | DNA phosphorothioate | CAGCAGCAGCAGCAGCAG (SEQ ID NO: 5) |
| PS259 | 2'OMe RNA phosphorothioate | ACGACGACGACGACGACG (SEQ ID NO: 20) |
| PS261 | 2'OMe RNA phosphorothioate | CIGCIGCIGCIGCIGCIG (SEQ ID NO: 6) |
| PS262 | 2'OMe RNA phosphorothioate | UCGUCGUCGUCGUCGUCG (SEQ ID NO: 7) |
| PS277 | Capitals: 2'OMe RNA phosphorothioate Lower case: DNA phosphorothioate | Gapmer: CUGCUgctgttgctgCUGCU (SEQ ID NO: 8) |
| PS278 | Capitals: 2'OMe RNA phosphorothioate Lower case: DNA phosphorothioate | Gapmer: CUGCUgctgctgctgCUGCU (SEQ ID NO: 9) |
| PI-01 | Double stranded RNA (siRNA) | 5'-CAGCAGCAGCAGCAGCA GCAG-3' (SEQ ID NO: 21) 3'-UCGUCGUCGUCGUCGUC GUCG-5'C (SEQ ID NO: 7) |
| PI-02 | Double stranded RNA (siRNA) | 5'-GCAGCAGCAGCAGCAGC AGCA-3' (SEQ ID NO: 19) 3'-GUCGUCGUCGUCGUCGU CGUC-5'C (SEQ ID NO: 23) |

TABLE 2 preferred oligonucleotides containing inosine and/or an uracile (i.e. a nucleotide containing a base able to form a wobble base pair)

| repeat | C | A | G | C | A | G | |
|---|---|---|---|---|---|---|---|
| oligo | G | U | C | G | U | C | 5'* |
| | G | U | U | G | U | U | 5' |
| | G | I | C | G | I | C | 5' |
| | G | I | U | G | I | U | 5' |
| | I | U | C | I | U | C | 5' |
| | I | U | U | I | U | U | 5' |
| | I | I | C | I | I | C | 5' |
| | I | I | U | I | I | U | 5' |

TABLE 2-continued preferred oligonucleotides containing inosine and/or an uracile (i.e. a nucleotide containing a base able to form a wobble base pair)

| repeat | C | U | G | C | U | G | |
|---|---|---|---|---|---|---|---|
| oligo | G | A | C | G | A | C | 5' |
| | G | A | U | G | A | U | 5' |
| | G | I | C | G | I | C | 5' |
| | G | I | U | G | I | U | 5' |
| | I | A | C | I | A | C | 5' |
| | I | A | U | I | A | U | 5' |
| | I | I | C | I | I | C | 5' |
| | I | I | U | I | I | U | 5' |

| repeat | C | G | G | C | G | G | |
|---|---|---|---|---|---|---|---|
| oligo | G | C | C | G | C | C | 5' |
| | G | C | U | G | C | U | 5' |
| | G | U | C | G | U | C | 5' |
| | G | U | U | G | U | U | 5' |
| | I | C | C | I | C | C | 5' |
| | I | C | U | I | C | U | 5' |
| | I | U | C | I | U | C | 5' |
| | I | U | U | I | U | U | 5' |

| repeat | G | C | G | G | C | G | |
|---|---|---|---|---|---|---|---|
| oligo | C | G | C | C | G | C | 5' |
| | C | G | U | C | G | U | 5' |
| | C | I | C | C | I | C | 5' |
| | C | I | U | C | I | U | 5' |
| | U | G | C | U | G | C | 5' |
| | U | G | U | U | G | U | 5' |
| | U | I | C | U | I | C | 5' |
| | U | I | U | U | I | U | 5' |

| repeat | G | A | A | G | A | A | |
|---|---|---|---|---|---|---|---|
| oligo | C | U | U | C | U | U | 5' |
| | C | U | I | C | U | I | 5' |
| | C | I | U | C | I | U | 5' |
| | C | I | I | C | I | I | 5' |
| | U | U | U | U | U | U | 5' |
| | U | U | I | U | U | I | 5' |
| | U | I | U | U | I | U | 5' |
| | U | I | I | U | I | I | 5' |

| repeat | G | C | C | G | C | C | |
|---|---|---|---|---|---|---|---|
| oligo | C | G | G | C | G | G | 5' |
| | C | G | I | C | G | I | 5' |
| | C | I | G | C | I | G | 5' |
| | C | I | I | C | I | I | 5' |
| | U | G | G | U | G | G | 5' |
| | U | G | I | U | G | I | 5' |
| | U | I | G | U | I | G | 5' |
| | U | I | I | U | I | I | 5' |

| repeat | C | C | U | G | C | C | U | G |
|---|---|---|---|---|---|---|---|---|
| oligo | G | G | A | C | G | G | A | C | 5' |
| | G | G | A | U | G | G | A | U | 5' |
| | G | G | I | C | G | G | I | C | 5' |
| | G | G | I | U | G | G | I | U | 5' |
| | G | I | A | C | G | I | A | C | 5' |
| | G | I | A | U | G | I | A | U | 5' |
| | G | I | I | C | G | I | I | C | 5' |
| | G | I | I | U | G | I | I | U | 5' |
| | I | G | A | C | I | G | A | C | 5' |
| | I | G | A | U | I | G | A | U | 5' |
| | I | G | I | C | I | G | I | C | 5' |
| | I | G | I | U | I | G | I | U | 5' |
| | I | I | A | C | I | I | A | C | 5' |
| | I | I | A | U | I | I | A | U | 5' |
| | I | I | I | C | I | I | I | C | 5' |
| | I | I | I | U | I | I | I | U | 5' |

*all the oligonucleotide sequences as given in these tables are to be read from right to left.

The invention claimed is:

1. An oligonucleotide comprising an inosine, wherein said oligonucleotide consists of a sequence that is complementary to a repetitive sequence selected from the group consisting of (CAG)n, (GCG)n, (CUG)n, (CGG)n, (GAA)n, (GCC)n and (CCUG)n, and is 9 to 50 nucleotides long.

2. An oligonucleotide according to claim 1, consisting of a sequence that is complementary to a repetitive sequence selected from the group consisting of (CAG)n, (GCG)n, (CUG)n, (CGG)n, (GAA)n, (GCC)n and (CCUG)n, wherein the oligoucleotide is 9 to 50 nucleotides long and wherein the oligonucleotide is a RNAse H substantially independent oligonucleotide.

3. An oligonucleotide according to claim 1, wherein said oligonucleotide comprises a radioactive label or fluorescent label.

4. An oligonucleotide according to claim 2, wherein said oligonucleotide comprises a radioactive label or fluorescent label.

5. A pharmaceutically acceptable composition comprising an oligonucleotide as defined in any one of claims 1 to 4 and at least one excipient and/or targeting ligand for delivery of the oligonucleotide to the cell and/or enhancing the intracellular delivery of the oligonucleotide.

6. A nucleic acid vector capable of conferring expression of an oligonucleotide as defined by any one of claims 1 to 4 in human cells.

7. An oligonucleotide according to any one of claims 1-4, wherein the oligonucleotide consists of $(CIG)_7$ and is a 2'-O-methyl RNA phosphorothioate oligonucleotide.

8. The nucleic acid vector of claim 6, wherein said vector is a viral vector.

* * * * *

SEQUENCE LISTING

<160> NUMBER OF SEQ ID NOS: 22

<210> SEQ ID NO 1
<211> LENGTH: 21
<212> TYPE: DNA
<213> ORGANISM: Artificial
<220> FEATURE:
<223> OTHER INFORMATION: primer flanking the repeat expansion region in
      exon 1-Forward

<400> SEQUENCE: 1
atggcgaccc tggaaaagct g                                              21

<210> SEQ ID NO 2
<211> LENGTH: 18
<212> TYPE: DNA
<213> ORGANISM: Artificial
<220> FEATURE:
<223> OTHER INFORMATION: primer flanking the repeat expansion region in
      exon 1

<400> SEQUENCE: 2
tgaggcagca gcggctgt                                                  18

<210> SEQ ID NO 3
<211> LENGTH: 21
<212> TYPE: RNA
<213> ORGANISM: Artificial
<220> FEATURE:
<223> OTHER INFORMATION: PS57, antisense oligonucleotide
<220> FEATURE:
<221> NAME/KEY: misc_feature
<223> OTHER INFORMATION: Backbone Modification: 2'OMe RNA
      phosphorothioate (with or without fluorescent FAM label)

<400> SEQUENCE: 3
cugcugcugc ugcugcugcu g                                              21

<210> SEQ ID NO 4
<211> LENGTH: 21
<212> TYPE: RNA
<213> ORGANISM: Artificial
<220> FEATURE:
<223> OTHER INFORMATION: PS58, antisense oligonucleotide
<220> FEATURE:
<221> NAME/KEY: misc_feature
<223> OTHER INFORMATION: Backbone Modification:2'OMe RNA
      phosphorothioate (with or without fluorescent FAM label)

<400> SEQUENCE: 4
cagcagcagc agcagcagca g                                              21

<210> SEQ ID NO 5
<211> LENGTH: 21
<212> TYPE: DNA
<213> ORGANISM: Artificial
<220> FEATURE:
<223> OTHER INFORMATION: PS142, antisense oligonucleotide
<220> FEATURE:
<221> NAME/KEY: misc_feature
<223> OTHER INFORMATION: Backbone Modification: DNA phosphorothioate

<400> SEQUENCE: 5
cagcagcagc agcagcagca g                                              21

<210> SEQ ID NO 6
<211> LENGTH: 21

```
<212> TYPE: RNA
<213> ORGANISM: Artificial
<220> FEATURE:
<223> OTHER INFORMATION: PS261, antisense oligonucleotide
<220> FEATURE:
<221> NAME/KEY: misc_feature
<223> OTHER INFORMATION: Backbone modification: 2'OMe RNA
      phosphorothioate
<220> FEATURE:
<221> NAME/KEY: modified_base
<222> LOCATION: (2)..(2)
<223> OTHER INFORMATION: N is equal to A or I
<220> FEATURE:
<221> NAME/KEY: modified_base
<222> LOCATION: (5)..(5)
<223> OTHER INFORMATION: N is equal to A or I
<220> FEATURE:
<221> NAME/KEY: modified_base
<222> LOCATION: (8)..(8)
<223> OTHER INFORMATION: N is equal to A or I
<220> FEATURE:
<221> NAME/KEY: modified_base
<222> LOCATION: (11)..(11)
<223> OTHER INFORMATION: N is equal to A or I
<220> FEATURE:
<221> NAME/KEY: modified_base
<222> LOCATION: (14)..(14)
<223> OTHER INFORMATION: N is equal to A or I
<220> FEATURE:
<221> NAME/KEY: modified_base
<222> LOCATION: (17)..(17)
<223> OTHER INFORMATION: N is equal to A or I
<220> FEATURE:
<221> NAME/KEY: modified_base
<222> LOCATION: (20)..(20)
<223> OTHER INFORMATION: N is equal to A or I

<400> SEQUENCE: 6
cngcngcngc ngcngcngcn g                                              21

<210> SEQ ID NO 7
<211> LENGTH: 21
<212> TYPE: RNA
<213> ORGANISM: Artificial
<220> FEATURE:
<223> OTHER INFORMATION: PS262, antisense oligonucleotide
<220> FEATURE:
<221> NAME/KEY: misc_feature
<223> OTHER INFORMATION: Backbone Modification: 2'OMe RNA
      phosphorothioate

<400> SEQUENCE: 7
ucgucgucgu cgucgucguc g                                              21

<210> SEQ ID NO 8
<211> LENGTH: 20
<212> TYPE: DNA
<213> ORGANISM: Artificial
<220> FEATURE:
<223> OTHER INFORMATION: PS277, antisense oligonucleotide
<220> FEATURE:
<221> NAME/KEY: misc_feature
<222> LOCATION: (1)..(5)
<223> OTHER INFORMATION: Backbone Modification: 2'OMe RNA
      phosphorothioate
<220> FEATURE:
<221> NAME/KEY: misc_feature
<222> LOCATION: (6)..(15)
<223> OTHER INFORMATION: Backbone Modification: DNA phosphorothioate
<220> FEATURE:
<221> NAME/KEY: misc_feature
<222> LOCATION: (16)..(20)
<223> OTHER INFORMATION: Backbone Modification: 2'OMe RNA
      phosphorothioate

<400> SEQUENCE: 8
```
cugcugctgt tgctgcugcu                                          20

<210> SEQ ID NO 9
<211> LENGTH: 20
<212> TYPE: DNA
<213> ORGANISM: Artificial
<220> FEATURE:
<223> OTHER INFORMATION: PS278, antisense oligonucleotide
<220> FEATURE:
<221> NAME/KEY: misc_feature
<222> LOCATION: (1)..(5)
<223> OTHER INFORMATION: Backbone Modification: 2'OMe RNA
      phosphorothioate
<220> FEATURE:
<221> NAME/KEY: misc_feature
<222> LOCATION: (6)..(15)
<223> OTHER INFORMATION: Backbone Modification: DNA phosphorothioate
<220> FEATURE:
<221> NAME/KEY: misc_feature
<222> LOCATION: (16)..(20)
<223> OTHER INFORMATION: Backbone Modification: 2'OMe RNA
      phosphorothioate

<400> SEQUENCE: 9
cugcugctgc tgctgcugcu                                          20

<210> SEQ ID NO 10
<211> LENGTH: 9
<212> TYPE: RNA
<213> ORGANISM: Artificial
<220> FEATURE:
<223> OTHER INFORMATION: chemically synthesized oligonucleotide (GCG)n

<400> SEQUENCE: 10 gcggcggcg                                                       9

<210> SEQ ID NO 11
<211> LENGTH: 9
<212> TYPE: RNA
<213> ORGANISM: Artificial
<220> FEATURE:
<223> OTHER INFORMATION: chemically synthesized oligonucleotide (CGG)n

<400> SEQUENCE: 11 cggcggcgg                                                       9

<210> SEQ ID NO 12
<211> LENGTH: 9
<212> TYPE: RNA
<213> ORGANISM: Artificial
<220> FEATURE:
<223> OTHER INFORMATION: chemically synthesized oligonucleotide (CCG)n

<400> SEQUENCE: 12 ccgccgccg                                                       9

<210> SEQ ID NO 13
<211> LENGTH: 9
<212> TYPE: RNA
<213> ORGANISM: Artificial
<220> FEATURE:
<223> OTHER INFORMATION: chemically synthesized oligonucleotide (GAA)n

<400> SEQUENCE: 13 gaagaagaa                                                       9

<210> SEQ ID NO 14
<211> LENGTH: 9

```
<212> TYPE: RNA
<213> ORGANISM: Artificial
<220> FEATURE:
<223> OTHER INFORMATION: chemically synthesized oligonucleotide (GCC)n

<400> SEQUENCE: 14 gccgccgcc                                                                  9

<210> SEQ ID NO 15
<211> LENGTH: 12
<212> TYPE: RNA
<213> ORGANISM: Artificial
<220> FEATURE:
<223> OTHER INFORMATION: chemically synthesized oligonucleotide (CCUG)n

<400> SEQUENCE: 15
ccugccugcc ug                                                             12

<210> SEQ ID NO 16
<211> LENGTH: 9
<212> TYPE: RNA
<213> ORGANISM: Artificial
<220> FEATURE:
<223> OTHER INFORMATION: chemically synthesized oliogonucelotide (CAG)n

<400> SEQUENCE: 16 cagcagcag                                                                  9

<210> SEQ ID NO 17
<211> LENGTH: 9
<212> TYPE: RNA
<213> ORGANISM: Artificial
<220> FEATURE:
<223> OTHER INFORMATION: chemically synthesized oliogonucelotide (CUG)n

<400> SEQUENCE: 17 cugcugcug                                                                  9

<210> SEQ ID NO 18
<211> LENGTH: 21
<212> TYPE: RNA
<213> ORGANISM: Artificial
<220> FEATURE:
<223> OTHER INFORMATION: chemically synthesized oliogonucelotide (CUG)7

<400> SEQUENCE: 18
cugcugcugc ugcugcugcu g                                                   21

<210> SEQ ID NO 19
<211> LENGTH: 21
<212> TYPE: RNA
<213> ORGANISM: Artificial
<220> FEATURE:
<223> OTHER INFORMATION: chemically synthesized oliogonucelotide (GCA)7

<400> SEQUENCE: 19
gcagcagcag cagcagcagc a                                                   21

<210> SEQ ID NO 20
<211> LENGTH: 21
<212> TYPE: RNA
<213> ORGANISM: artificial
<220> FEATURE:
<223> OTHER INFORMATION: oligonucleotide

<400> SEQUENCE: 20
acgacgacga cgacgacgac g                                                   21
```

```
<210> SEQ ID NO 21
<211> LENGTH: 21
<212> TYPE: RNA
<213> ORGANISM: artificial
<220> FEATURE:
<223> OTHER INFORMATION: oligonucleotide

<400> SEQUENCE: 21
cagcagcagc agcagcagca g                                              21

<210> SEQ ID NO 22
<211> LENGTH: 21
<212> TYPE: RNA
<213> ORGANISM: artificial
<220> FEATURE:
<223> OTHER INFORMATION: oligonucleotide

<400> SEQUENCE: 22
gcagcagcag cagcagcagc a                                              21
```